US011007262B2

(12) United States Patent
Watanabe et al.

(10) Patent No.: US 11,007,262 B2
(45) Date of Patent: *May 18, 2021

(54) VACCINES COMPRISING MUTANT ATTENUATED INFLUENZA VIRUSES

(71) Applicant: Wisconsin Alumni Research Foundation (WARF), Madison, WI (US)

(72) Inventors: Shinji Watanabe, Tokyo (JP); Tokiko Watanabe, Tokyo (JP); Yoshihiro Kawaoka, Middleton, WI (US)

(73) Assignee: Wisconsin Alumni Research Foundation (WARF), Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/173,605

(22) Filed: Oct. 29, 2018

(65) Prior Publication Data

US 2019/0117759 A1    Apr. 25, 2019

Related U.S. Application Data

(63) Continuation of application No. 13/070,110, filed on Mar. 23, 2011, now Pat. No. 10,130,697.

(60) Provisional application No. 61/316,564, filed on Mar. 23, 2010.

(51) Int. Cl.
*A61K 39/12* (2006.01)
*A61K 39/145* (2006.01)
*C12N 7/00* (2006.01)
*A61K 39/00* (2006.01)

(52) U.S. Cl.
CPC ...... *A61K 39/12* (2013.01); *A61K 2039/5254* (2013.01); *A61K 2039/543* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 4,071,618 A | 1/1978 | Konobe et al. | |
| 4,659,569 A | 4/1987 | Mitsuhashi et al. | |
| 5,166,057 A | 11/1992 | Palese et al. | |
| 5,716,821 A | 2/1998 | Wertz et al. | |
| 5,789,229 A | 8/1998 | Wertz et al. | |
| 5,820,871 A | 10/1998 | Palese et al. | |
| 5,840,520 A | 11/1998 | Clarke et al. | |
| 5,854,037 A | 12/1998 | Palese et al. | |
| 5,948,410 A | 9/1999 | Van Scharrenburg et al. | |
| 5,994,526 A | 11/1999 | Meulewaeter et al. | |
| 6,033,886 A | 3/2000 | Conzelmann | |
| 6,037,348 A | 3/2000 | Colacino et al. | |
| 6,146,642 A | 11/2000 | Garcia-Sastre et al. | |
| 6,169,175 B1 | 1/2001 | Frace et al. | |
| 6,194,546 B1 | 2/2001 | Newton et al. | |
| 6,455,298 B1 | 9/2002 | Groner et al. | |
| 6,544,785 B1 | 4/2003 | Palese et al. | |
| 6,656,720 B2 | 12/2003 | Groner et al. | |
| 6,825,036 B2 | 11/2004 | Makizumi et al. | |
| 6,872,395 B2 | 3/2005 | Kawaoka | |
| 6,951,752 B2 | 10/2005 | Reiter et al. | |
| 6,951,754 B2 | 10/2005 | Hoffmann | |
| 6,974,695 B2 | 12/2005 | Vogels et al. | |
| 7,037,707 B2 | 5/2006 | Webster et al. | |
| 7,176,021 B2 | 2/2007 | Kawaoka | |
| 7,226,774 B2 | 6/2007 | Kawaoka | |
| 7,312,064 B2 | 12/2007 | Hoffmann | |
| 7,507,411 B2 | 3/2009 | Zhou et al. | |
| 7,566,458 B2 | 7/2009 | Yang et al. | |
| 7,585,657 B2 | 9/2009 | Kawaoka | |
| 7,588,769 B2 | 9/2009 | Kawaoka | |
| 7,670,837 B2 | 3/2010 | Schwartz | |
| 7,833,788 B2 | 11/2010 | Pau et al. | |
| 7,883,844 B2 | 2/2011 | Nouchi et al. | |
| 7,955,833 B2 | 6/2011 | Reiter et al. | |
| 7,959,930 B2 | 6/2011 | De Wit et al. | |
| 7,972,843 B2 | 7/2011 | Hoffmann | |
| 7,993,924 B2 | 8/2011 | Billeter et al. | |
| 8,012,736 B2 | 9/2011 | Hoffman et al. | |
| 8,048,430 B2 | 11/2011 | Yang et al. | |
| 8,057,806 B2 | 11/2011 | Kawaoka | |
| 8,093,033 B2 | 1/2012 | Kemble et al. | |
| 8,114,415 B2 | 2/2012 | Hoffmann et al. | |
| 8,119,337 B2 | 2/2012 | Gregersen | |
| 8,119,388 B2 | 2/2012 | Schwartz et al. | |
| 8,309,099 B2 | 11/2012 | Hoffmann | |
| 8,354,114 B2 | 1/2013 | Lu et al. | |
| 8,357,376 B2 | 1/2013 | Liu et al. | |
| 8,409,843 B2 | 4/2013 | Kemble et al. | |
| 8,460,914 B2 | 6/2013 | Gregersen | |
| 8,475,806 B2 | 7/2013 | Kawaoka | |
| 8,524,497 B2 | 9/2013 | Reiter et al. | |
| 8,546,123 B2 | 10/2013 | Lewis | |
| 8,574,591 B2 | 11/2013 | Hoffmann et al. | |
| 8,574,593 B2 | 11/2013 | Yang et al. | |
| 8,580,277 B2 | 11/2013 | Yang et al. | |
| 8,591,914 B2 | 11/2013 | Yang et al. | |

(Continued)

FOREIGN PATENT DOCUMENTS

| | | | |
|---|---|---|---|
| AU | 2012204138 B2 | 5/2014 | |
| CN | 1826407 B | 9/2013 | |

(Continued)

OTHER PUBLICATIONS

Result 17, NCBI Blast nucleotide search of SEQ ID No. 2, database "nr", (Jul. 18, 2006), 3 pgs.

(Continued)

*Primary Examiner* — Stacy B Chen
(74) *Attorney, Agent, or Firm* — Schwegman Lundberg & Woessner, P.A.

(57) ABSTRACT

The invention provides a vaccine comprising an effective amount of an isolated recombinant influenza virus comprising a mutant M gene segment that is mutated so that upon viral replication the mutant M gene expresses a functional M1 protein and a mutant M2 protein with a deletion of the cytoplasmic tail and either lacking a transmembrane domain or having a mutated transmembrane domain.

26 Claims, 12 Drawing Sheets

Specification includes a Sequence Listing.

(56) References Cited

U.S. PATENT DOCUMENTS

| | | | |
|---|---|---|---|
| 9,254,318 B2 | 2/2016 | Kawaoka et al. | |
| 9,284,533 B2 | 3/2016 | Bilsel et al. | |
| 9,474,798 B2 | 10/2016 | Watanabe et al. | |
| 9,757,446 B2 | 9/2017 | LeFebvre et al. | |
| 9,950,057 B2 | 4/2018 | Kawaoka et al. | |
| 10,130,697 B2* | 11/2018 | Watanabe | A61K 39/12 |
| 10,172,934 B2 | 1/2019 | Kawaoka et al. | |
| 2002/0164770 A1 | 11/2002 | Hoffmann | |
| 2002/0197705 A1 | 12/2002 | Kawaoka | |
| 2003/0035814 A1 | 2/2003 | Kawaoka et al. | |
| 2003/0044962 A1 | 3/2003 | Makizumi et al. | |
| 2003/0073223 A1 | 4/2003 | Groner et al. | |
| 2003/0119183 A1 | 6/2003 | Groner | |
| 2003/0194694 A1 | 10/2003 | Kawaoka | |
| 2004/0002061 A1 | 1/2004 | Kawaoka | |
| 2004/0063141 A1 | 4/2004 | Lok | |
| 2004/0077086 A1 | 4/2004 | Reiter et al. | |
| 2004/0219170 A1 | 11/2004 | Kawaoka | |
| 2005/0003349 A1 | 1/2005 | Kawaoka | |
| 2005/0037487 A1 | 2/2005 | Kawaoka et al. | |
| 2005/0118140 A1 | 6/2005 | Vorlop et al. | |
| 2005/0158342 A1 | 7/2005 | Kemble et al. | |
| 2005/0186563 A1 | 8/2005 | Hoffmann | |
| 2005/0202553 A1 | 9/2005 | Groner et al. | |
| 2005/0232950 A1 | 10/2005 | Kawaoka | |
| 2005/0266026 A1 | 12/2005 | Hoffmann et al. | |
| 2006/0057116 A1 | 3/2006 | Kawaoka et al. | |
| 2006/0166321 A1 | 7/2006 | Kawaoka et al. | |
| 2006/0188977 A1 | 8/2006 | Schwartz et al. | |
| 2006/0246092 A1 | 11/2006 | Neirynck et al. | |
| 2007/0231348 A1 | 10/2007 | Kawaoka et al. | |
| 2008/0233560 A1 | 9/2008 | Hoffmann | |
| 2008/0254067 A1 | 10/2008 | Trepanier et al. | |
| 2008/0274141 A1 | 11/2008 | Groner et al. | |
| 2008/0311148 A1 | 12/2008 | Hoffmann | |
| 2008/0311149 A1 | 12/2008 | Hoffmann | |
| 2009/0074812 A1 | 3/2009 | Watanabe et al. | |
| 2009/0081252 A1 | 3/2009 | Gregersen | |
| 2009/0181446 A1 | 7/2009 | Nouchi et al. | |
| 2010/0112000 A1 | 5/2010 | Schwartz | |
| 2010/0183671 A1 | 7/2010 | Gregersen et al. | |
| 2010/0247572 A1 | 9/2010 | Kawaoka | |
| 2011/0027314 A1 | 2/2011 | Broeker | |
| 2011/0045022 A1 | 2/2011 | Tsai | |
| 2011/0110978 A1 | 5/2011 | Kawaoka et al. | |
| 2011/0236417 A1 | 9/2011 | Watanabe et al. | |
| 2012/0020997 A1 | 1/2012 | Hoffman et al. | |
| 2012/0034600 A1 | 2/2012 | Gregersen | |
| 2012/0115206 A1 | 5/2012 | Schwartz et al. | |
| 2012/0156241 A1 | 6/2012 | De Wit et al. | |
| 2012/0207785 A1 | 8/2012 | Fabry et al. | |
| 2013/0095135 A1 | 4/2013 | Collignon et al. | |
| 2013/0183741 A1 | 7/2013 | Park et al. | |
| 2013/0316434 A1 | 11/2013 | Reiter et al. | |
| 2015/0017205 A1 | 1/2015 | Kawaoka et al. | |
| 2016/0208223 A1 | 7/2016 | Kawaoka et al. | |
| 2017/0096645 A1 | 4/2017 | Watanabe et al. | |
| 2017/0354730 A1 | 12/2017 | Kawaoka et al. | |

FOREIGN PATENT DOCUMENTS

| | | | |
|---|---|---|---|
| EP | 0702085 A1 | 3/1996 | |
| EP | 1201760 A1 | 5/2002 | |
| EP | 2010557 B1 | 2/2014 | |
| EP | 1631663 B1 | 8/2016 | |
| IL | 171831 A | 5/2015 | |
| JP | 2004500842 A | 1/2004 | |
| JP | 2005523698 A | 8/2005 | |
| JP | 2005245302 A | 9/2005 | |
| JP | 2005535288 A | 11/2005 | |
| JP | 2009532352 A | 9/2009 | |
| JP | 4927290 B2 | 2/2012 | |
| JP | 4927290 | 5/2012 | |
| JP | 2014039551 A | 3/2014 | |
| JP | 2014131516 A | 7/2014 | |
| JP | 2016524915 A | 8/2016 | |
| JP | 2016169225 A | 9/2016 | |
| MX | 285206 | 3/2011 | |
| WO | WO-9610631 A1 | 4/1996 | |
| WO | WO-9610632 A1 | 4/1996 | |
| WO | WO-9640955 A1 | 12/1996 | |
| WO | WO-9737000 A1 | 10/1997 | |
| WO | WO-9802530 A1 | 1/1998 | |
| WO | WO-9853078 A1 | 11/1998 | |
| WO | WO-9928445 A1 | 6/1999 | |
| WO | WO-0053786 A1 | 9/2000 | |
| WO | WO-0060050 A2 | 10/2000 | |
| WO | WO-2000060050 A2 | 10/2000 | |
| WO | WO-0060050 A3 | 1/2001 | |
| WO | WO-0179273 A2 | 10/2001 | |
| WO | WO-0183794 A2 | 11/2001 | |
| WO | WO-2001083794 A2 | 11/2001 | |
| WO | WO-03068923 A2 | 8/2003 | |
| WO | WO-2003068923 A2 | 8/2003 | |
| WO | WO-03076462 A1 | 9/2003 | |
| WO | WO-03091401 A2 | 11/2003 | |
| WO | WO-2003091401 A2 | 11/2003 | |
| WO | WO-04094466 A2 | 11/2004 | |
| WO | WO-2004094466 A2 | 11/2004 | |
| WO | WO-04112831 A2 | 12/2004 | |
| WO | WO-2004112831 A2 | 12/2004 | |
| WO | WO-2004112831 A3 | 12/2004 | |
| WO | WO-2005062820 A2 | 7/2005 | |
| WO | WO-2007126810 A2 | 11/2007 | |
| WO | WO-2007126810 A3 | 11/2007 | |
| WO | WO-2008156778 A2 | 12/2008 | |
| WO | WO-2008156778 A3 | 12/2008 | |
| WO | WO-2008156778 A9 | 2/2009 | |
| WO | WO-2011056591 A1 | 5/2011 | |
| WO | WO-2012177924 A2 | 12/2012 | |
| WO | WO-2015009743 A1 | 1/2015 | |

OTHER PUBLICATIONS

Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.

Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.

Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.

Result 7, NCBI Blast nucleotide search of SEQ ID: 1, database "nr", (Jul. 18, 2006), 3 pgs.

FLUMISTTM Package Insert Template, [Online]. Retrieved from the Internet: http://www.fda.gov/downloads/BiologicsBioodVaccines!Vaccines/ApprovedProducts/UCM294307.pdf, (Mar. 1, 2012), 26 pgs.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 09/834,095, Advisory Action dated Jan. 8, 2004", 3 pgs.

"U.S. Appl. No. 09/834,095, Final Office Action dated Aug. 26, 2003", 12 pgs.

"U.S. Appl. No. 09/834,095, Non-Final Office Action dated Nov. 4, 2002", 12 pgs.

"U.S. Appl. No. 09/834,095, Notice of Allowance dated Sep. 27, 2004", 13 pgs.

"U.S. Appl. No. 09/834,095, Office Action dated Apr. 20, 2004", 11 pgs.

"U.S. Appl. No. 09/834,095, Response filed Feb. 4, 2003 to Office Action dated Nov. 4, 2002", 14 pgs.

"U.S. Appl. No. 09/834,095, Response filed Jun. 12, 2003 to Restriction Requirement dated Apr. 22, 2003", 2 pgs.

(56) References Cited

OTHER PUBLICATIONS

"U.S. Appl. No. 09/834,095, Response filed Jun. 18, 2004 to Office Action dated Apr. 20, 2004", 11 pgs.
"U.S. Appl. No. 09/834,095, Response filed Aug. 1, 2002 to Restriction Requirement dated Jul. 1, 2002", 3 pgs.
"U.S. Appl. No. 09/834,095, Response filed Nov. 26, 2003 to Final Office Action dated Aug. 26, 2003", 10 pgs.
"U.S. Appl. No. 09/834,095, Restriction Requirement dated Apr. 22, 2003", 5 pgs.
"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", FOAR, 20 Pgs.
"U.S. Appl. No. 10/855,875, Final Office Action dated Dec. 10, 2010", 15 pgs.
"U.S. Appl. No. 10/855,875, Final Office Action dated Aug. 2, 2006", 34 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Non-Final Office Action dated May 3, 2007", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010". 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response filed Dec. 7, 2009 to Non Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007", 16 pgs.
"U.S. Appl. No. 11/043,768 Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non Final Office Action dated Feb. 23, 2010", 9 pgs.
"U.S. Appl. No. 11/043,768, Response filed Jun. 23, 2009 to Non Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non Final Office Action dated Feb. 18, 2015", 13 pgs.
"U.S. Appl. No. 11/729,557, Non Final Office Action dated Feb. 26, 2014", 16 pgs.
"Application U.S. Appl. No. 11/729,557, Non-Final Office Action mailed 01-30-09", 20 pgs.
"Application U.S. Appl. No. 11/729,557, Non-Final Office Action mailed 02-22-10", 16 pgs.
"Application U.S. Appl. No. 11/729,557, Non-Final Office Action mailed 08-23-10", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.

(56) References Cited

OTHER PUBLICATIONS

"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.
"U.S. Appl. No. 11/729,557, Response filed Oct. 28, 2010 to Non Final Office Action dated Aug. 23, 2010", 13 pgs
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"U.S. Appl. No. 12/214,414, Advisory Action dated Feb. 2, 2016", 5 pgs.
"U.S. Appl. No. 12/214,414, Advisory Action dated Apr. 15, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.
"U.S. Appl. No. 12/214,414, Final Office Action dated Nov. 18, 2015", 17 pgs.
"U.S. Appl. No. 12/214,414, Non Final Office Action dated Jun. 12, 2014", 28 pgs.
"U.S. Appl. No. 12/214,414, Non Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.
"U.S. Appl. No. 12/214,414, Response filed May 3, 2011 to Non Final Office Action dated Dec. 10, 2010", 12 pgs.
"U.S. Appl. No. 12/214,414, Response flied Jul. 20, 2015 to Advisory Action dated Apr. 15, 2015", 14 pgs.
"U.S. Appl. No. 12/214,414, Response filed Aug. 31, 2010 to Non Final Office Action dated Mar. 2, 2010", 11 pgs.
"U.S. Appl. No. 12/214,414, Response filed Oct. 3, 2011 to Non Final Office Action dated Aug. 2, 2011", 9 pgs.
"U.S. Appl. No. 12/214,414, Response filed Dec. 21, 2011 to Advisory Action dated Oct. 21, 2011", 10 pgs.
"U.S. Appl. No. 12/467,492, Restriction Requirement dated Nov. 22, 2010", 6 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.
"U.S. Appl. No. 12/912,411, Non Final Office Action dated Sep. 24, 2014", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 13/070,110 Response filed Feb. 14, 2017 to Final Office Action dated Sep. 14, 2016", 8 pgs.
"U.S. Appl. No. 13/070,110, Advisory Action dated Mar. 3, 2017", 5 pgs.
"U.S. Appl. No. 13/070,110, Examiner Interview Summary dated Jan. 16, 2018", 3 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.
"U.S. Appl. No. 13/070,110, Final Office Action dated Sep. 14, 2016", 12 pgs.
"U.S. Appl. No. 13/070,110, Non Final Office Action dated Jul. 21, 2017", 14 pgs.
"U.S. Appl. No. 13/070,110, Non Final Office Action dated Oct. 2, 2014", 24 pgs.
"U.S. Appl. No. 13/070,110, Non Final Office Action dated Dec. 11, 2015", 19 pgs.
"U.S. Appl. No. 13/070,110, Non Final Office Action dated Dec. 21, 2012", 7 pgs.
"U.S. Appl. No. 13/070,110, Notice of Allowance dated Mar. 26, 2018", 6 pas.
"U.S. Appl. No. 13/070,110, Notice of Allowance dated Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication dated Aug. 15, 2018", 2 pgs.
"U.S. Appl. No. 13/070,110, Response filed Jan. 22, 2018 to Non Final Office Action dated Jul. 21, 2017", 10 pgs.
"U.S. Appl. No. 13/070,110, Response filed Mar. 22, 2013 to Non Final Office Action dated Dec. 21, 2012", 8 pgs.
"U.S. Appl. No. 13/070,110, Response filed May 27, 2016 to Non Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed Sep. 3, 2014 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 12, 2013 to Final Office Action dated Jun. 12, 2013", 9 pgs.
"U.S. Appl. No. 13/070,110, Response filed Dec. 30, 2014 to Non Final Office Action dated Oct. 2, 2014", 13 pgs.
"U.S. Appl. No. 13/070,110, Restriction Requirement dated Jul. 8, 2014", 7 pgs.
"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.

(56) References Cited

OTHER PUBLICATIONS

"U.S. Appl. No. 14;332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 15/000,851, Preliminary Amendment filed Feb. 3, 2016", 3 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/292,595, Non Final Office Action dated Sep. 25, 2017", 13 pgs.
"U.S. Appl. No. 15/292,595, Notice of Allowance dated Feb. 28, 2018", 9 pgs.
"U.S. Appl. No. 15/292,595, Notice of Allowance dated Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action dated Sep. 25, 2017", 9 pgs.
"U.S. Appl. No. 15/593,039, Non Final Office Action dated Feb. 6, 2018", 8 pgs.
"U.S. Appl. No. 15/593,039, Preliminary Amendment filed Jul. 25, 2017", 7 pgs.
"U.S. Appl. No. 15/593,039, Response filed Apr. 30, 2018 to Non Final Office Action dated Feb. 4, 2018", 8 pas.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017".
"Application Serial No. 200480021259.9 Office Action Sep. 11, 2009", 7 pgs.
"Application Serial No. 200480021259.9 Office Action Response Filed Aug. 20, 2010", 26 pgs.
"Application Serial No. 2006-533439 Office Action dated Mar. 9, 2010", 20 pgs.
"U.S. Appl. No. 12/214,414, Response filed Oct. 14, 2014 to Non Final Office Action dated Jun. 12, 2014", 16 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Respojnse filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Brazilian Application Serial No. PI0410702-0, Office Action dated Feb. 23, 2012", (w/ English Translation), 4 pgs.
"Brazilian Application Serial No. PI0410702-0, Response filed May 7, 2012 to Office Action dated Feb. 23, 2012", (w/ English Translation of Claims), 11 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,522,081, Amendment After Allowance filed Aug. 10, 2012", 3 Pgs.
"Canadian Application Serial No. 2,522,081, Office Action filed Nov. 18, 2011", 11 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2,525,953, Office Action dated Jan. 21, 2016", 6 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Dec. 22, 2011 to Office Action dated Jun. 22, 2011", 17 pgs.
"Canadian Application Serial No. 2,647,985 , Office Action dated May 15, 2013", 3 pgs.
"Canadian Application Serial No. 2,647,985 , Response filed Sep. 30, 2013 to Office Action dated May 15, 2013", 20 pgs.
"Canadian Application Serial No. 2406180, Response filed May 7, 2012 to Office Action dated Nov. 10, 2011", 11 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.

(56) References Cited

OTHER PUBLICATIONS

"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9, Notice of Reexamination dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action", (w/ English Translation of Claims), 13 pgs.
"Eurasian Application Serial No. 200501890, Response filed Dec. 17, 2008 to Office Action dated Sep. 4, 2008", (w/ English Translation of Claims), 14 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication dated Oct. 12, 2006", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons to Attend Oral Proceedings dated Aug. 3, 2011", 13 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.
"European Application Serial No. 04776133.3, Response filed Sep. 18, 2015 to Examination Notification Art. 94(3) dated Jul. 28, 2015", 47 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.

(56) References Cited

OTHER PUBLICATIONS

"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Examination Notification Art, 94(3) dated Oct. 6, 2014", 7 pgs
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"European Application Serial No. 14745060.5, Office Action dated Feb. 23, 2016", 2 pgs.
"Evaluation of Medicines for human Use", EMEA/CPMP/BWP/2289/01, London, The European Agency for the Evaluation of Medicinal Products, Committee for Proprietary Medicinal Products (CPMP), (Feb. 20, 2003), 14.
"FLUZONE® Influenza Virus Vaccine", Sanofi Aventis Pasteur, Swiftwater, (Jul. 2005), 12 pgs.
"Hemagglutinin [Influenza A virus (A/swine/France/WVL13/1995(1-11N1))1", GenBank Accession# AC025026, (May 22, 2009), 1 pg.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Influenza B/lee/40, neuraminidase & nb (seg 6) rna", Database EM_V1 E.B.I. Hinxton U.K., (Jun. 13, 1985), 10 pgs.
"International Application No. PCT/US2004/016680, International Search Report"(dated Feb. 2, 2005), 7 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 2 pgs.
"International Application Serial No. PCT/US01/11963, Written Opinion dated Aug. 7, 2002", 6 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016680, International Preliminary Report on Patentability dated Dec. 15, 2005", 11 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2008/007582, International Preliminary Report on Patentability dated Jan. 7, 2010", 9 pgs.
"International Application Serial No. PCT/US2008/007582, International Search Report and Written Opinion dated Feb. 18, 2009", 16 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"International Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"Israeli Application Serial No. 171831, Notification of Defects dated Nov. 10, 2008", (English Translation), 10 pgs.
"Israeli Application Serial No. 171372, Office Action dated Feb. 21, 2010", (Translation), 2 pgs.
"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", (Translation), 19 pgs.
"Israeli Application Serial No. 171831, Office Action dated Feb. 21, 2010", (English Translation), 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", (English Translation), 18 pgs.
"Israeli Application Serial No. 171831, Response filed Jun. 24, 2009 to Notification of Defects dated Nov. 10, 2008", (w/ English Translation of Claims), 10 pgs.
"Israeli Application U.S. Appl. No. 171831, Response filed Nov. 6, 2012 to Office Action dated Apr. 18, 2012", (w/ English Translation of Amended Claims), 54 pgs.
"Israeli Application Serial No. 238584, Office Action dated Apr. 14, 2016", (English Translation), 3 pgs.
"Israeli Application Serial No. 238584, Response filed Aug. 3, 2016 to Office Action dated Apr. 14, 2016", (English Translation of Claims), 19 pgs.
"Israeli Application Serial No. 171372,Office Action dated Feb. 20, 2011", (Translation), 2 pgs.
"Japanese Application No. 2001-576868, Office Action dated May 31, 2011", (w/ English Translation), 5 pgs.
"Japanese Application No. 2001-576868, Response filed Apr. 26, 2011 to Office Action dated Nov. 2, 2010", (w/ Translation of Amended Claims), 14 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.

(56) References Cited

OTHER PUBLICATIONS

"Japanese Application Serial No. 2006-533439, Decision of Final Rejection dated Aug. 14, 2012", (w/ English Translation), 5 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439,Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.
"Japanese Application Serial No. 2009-502945, Response filed Apr. 10, 2013 to Office Action dated Oct. 23, 2012", (w/ English Translation of Claims), 18 pgs.
"Japanese Application Serial No. 2011-111048, Office Action dated Jun. 25, 2013", (w/ English Translation), 7 pgs.
"Japanese Application Serial No. 2011-111048, Office Action dated Sep. 18, 2012", (w/ English Translation), 10 pga.
"Japanese Application Serial No. 2011-111048, Response filed Sep. 25, 2012 to Office Action dated Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action dated Jan. 6, 2015", (w/ English Translation), 9 pgs.
"Japanese Application Serial No. 2014-049025 Response filed Sep. 4, 2015 to Office Action dated Jun. 16, 2015", (w/ Amended Claims), 12 pgs.
"Japanese Application Serial No. 2014-049025, Examiners Decision of Final Refusal dated Feb. 2, 2016", W/ English Translation, 5 pgs.
"Japanese Application Serial No. 2014-049025, Office Action dated Jun. 16, 2015", (w/ English Translation), 6 pgs.
"Japanese Application Serial No. 2006-513125,Final Office Action dated Jan. 18, 2011", Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 2007 to Notice of Preliminary Rejection dated Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", W/ English Claims, 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 18 pgs.
"Mexican Application Serial No. PA/a/2005/011250, Office Action dated Aug. 23, 2010", W/ English Translation, 4 pgs.
"Mexican Application Serial No. PA/a/2005/011250, Response Filed Dec. 20, 2010 to Office Action dated Aug. 23, 2010", (w/ English Translation of Claims), 14 pgs.
"Mexican Application Serial No. PA/a/2005/012712 , Office Action dated Aug. 11, 2009", (English Translation), 5 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Jun. 9, 2010", (w/ English Translation), 11 pgs.
"Mexican Application Serial No. PA/a/20051012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexican Application Serial No. PA/a/2005/012712, Response filed Sep. 27, 2010 to Office Action dated May 12, 2010", (w/ English Translation of Claims), 19 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report dated Feb. 29, 2008", 2 pgs.
"New Zealand Application Serial No. 543446, Examination Report dated May 12, 2008", 2 pgs.
"New Zealand Application Serial No. 543446, Response dated Mar. 20, 2008 to Examination Report dated Feb. 29, 2008", 2 pgs.
"Russian Federation Application No. 2005136233, Office Action dated Dec. 25, 2007", 2 pgs.
"Russian Federation Application No. 2005136233, Response filed May 29, 2008 to Office Action dated Dec. 25, 2007", (w/ Partial English Translation), 7 pas.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.

(56) References Cited

OTHER PUBLICATIONS

"Russian Federation Application Serial No. 2005136233, Response filed Nov. 20, 2007 to Office Action", (w/ English Translation of Amended Claims), 18 pgs.

"Singaporean Application Serial No. 200506858-0, Examination Report dated Feb. 9, 2007", 4 pgs.

"Singaporean Application Serial No. 200506858-0, Response filed Dec. 22, 2006 to Written Opinion dated Jul. 26, 2006", 18 pgs.

"Singaporean Application Serial No. 200506858-0, Written Opinion dated Jul. 26, 2006", 8 pgs.

"Singaporean Application Serial No. 200507468-7, Examination Report dated Mar. 19, 2008", 5 pgs.

"Singaporean Application Serial No. 200507468-7, Invitation to Respond to Written Opinion dated Jun. 12, 2007", 6 pgs.

"Singaporean Application Serial No. 200507468-7, Response filed Nov. 7, 2007 to Invitation to Respond to Written Opinion dated Jun. 12, 2007", 9 pgs.

"The Influenza Virus: Structure and Replication", Rapid Reference to Influenza. Elsevier Ltd, [Online]. Retrieved from the Internet: http://www.rapidreferenceinfluenza.com/chapter/B978-0/7234-3433-7.50009-8/aim/influenza-virus-structure, (2006), 6 pgs.

"The Integral Membrane Proteins of Influenza A, B, and C Viruses", The Influenza Sequence Database, http://www.flu.lanl.gov/review/fluc.review2.html, (Observed Feb. 26, 2003), 1 pg.

"Ukrainian Application Serial No. 200512619, Office Action dated Feb. 27, 2009", (w/ English Translation), 21 pgs.

"Ukrainian Application Serial No. 200512619, Office Action dated Jun. 17, 2009", (w/ English Translation), 4 pgs.

"Ukrainian Application Serial No. 200512619, Response filed Apr. 8, 2009 to Office Action dated Feb. 27, 2009", (w/ English Translation of Claims), 9 pgs.

Air, Gillian M., et al., "Antigenic, Sequence, and Crystal Variation in Influenza B Neuraminidase", Virology, 177(2), (1990), 578-587.

Author Unknown, "New Approaches to Influenza Vaccine", Medscape—Infections in Medicine, http://www.medscape.com/viewarticle/417404_3, (Observed Feb. 26, 2003), 4 pgs.

Avetisyan, G, et al., "Cell-mediated immune responses to influenza vaccination in healthy volunteers and allogeneic stem cell transplant recipients", Bone Marrow Transplant, (2005), 411-415.

Baez, M., et al., "Complete nucleotide sequence of the influenza A/PR/8/34. virus NS gene and comparison with the NS genes of the A/Udorn/72 and A/FPV/Rostock/34 strains", Nucleic Acids Research, 23(8), (1980), 5845-5858.

Bancroft, C. T, et al., "Evidence for segment-nonspecific packaging of the influenza a virus genome", J Virol., 76(14), (Jul. 2002), 7133-9.

Banerjee, A. K., et al., "Gene Expression of Vesicular Stomatitis Virus Genome RNA.", Virology, 188(2), 1992), 417-428.

Baron, M. D., et al., "Rescue of Rinderpest Virus From Cloned cDNA", Journal of Virology, 71(2),(1997), 1265-1271.

Basler, C. F, et al., "Mutation of Neuraminidase Cysteine Residues Yields Temperature-Sensitive Influenza Viruses", Journal of Virology, 73(10), (Jun. 30, 1999), 8095-8103.

Beare, A. S., "Trials in Man With Live Recombinants Made From A/PR/8/34 (H0 N1) and Wild H3 N2 Influenza Viruses", The Lancet, 2(7938), (1975), 729-732.

Betakova, T., et al., "The NB protein is an integral component of the membrane of influenza B virus.", J Gen Virol., 77 ( Pt 11), (Nov. 1996), 2689-94.

Bourmakina, S. V, et al., "Reverse genetics studies on the Filamentous morphology of influenza A Virus", Journal of General Virology (2003) 84,, (2003), 517-527.

Bowie, J. U., et al., "Deciphering the Message in Protein Sequences: Tolerance to Amino Acid Substitutions", Science, 247(4948), (1990), 1306-1310.

Boyer, J. C., et al., "Infectious transcripts and cDNA clones of RNA viruses", Virology, 198(2), (Feb. 1994), 415-426.

Brassard, D.L., et al., "Influenza B virus NB glycoprotein is a component of the virion", Viral., 220(2), No Document, (1996), 350-360.

Bridgen, A., "Rescue of a Segmented Negative-Strand RNA Virus Entirely From Cloned Complementary DNAs", Proc. Natl. Acad. Sci. USA, 93, (1996), 15400-15404.

Brooke, C B, "Biological activities of 'noninfectious' influenza A virus particles", Future Virol 9(1), (Jan. 2014), 41-51.

Brown, E. G., et al., "Genetic analysis of mouse-adapted influenza A virus identifies roles for the NA, PB1, and PB2 genes in virulence", Virus Research, 61(1), (May 1999), 63-76.

Buchholz, U. J., et al., "Generation of Bovine Respiratory Syncytial Virus (BRSV) From cDNA: BRSV NS2 is Not Essentilal for Virus Replication in Tissue Culture, and the Human RSV Leader Region Acts as a Functional BRSV Genome Promoter", Journal of Virology, 73(1), (1999), 251-259.

Bukreyev, A., et al., "Recovery of infectious respiratory syncytial virus expressing an additional, foreign gene", Journal of Virology, 70(10), (Oct. 1996), 6634-6641.

Castrucci, Maria R., et al., "Reverse genetics system for generation of an influenza A virus mutant containing a deletion of the carboxyl-terminal residue of M2 protein.", J Virol., 69(5), (May 1995), 2725-8.

Chen, H, et al., "Generation and evaluation of a high-growth reassortant H9N2 influenza A virus as a pandemic vaccine candidate", Vaccine, 21(17-18), (May 16, 2003), 1974-9.

Chen, Z., et al., "Influenza A Virus NS1 Protein Targets Poly(A)-Binding Protein II of the Cellular 3'-End Processing Machinery", The EMBO Journal, 18(8), (1999), 2273-2283.

Clarke, D. K., et al., "Rescue of Mumps Virus From cDNA", Journal of Virology, 74(10), (2000), 4831-4838.

Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.

Collins P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.

Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.

Conzelmann, K.-K., "Genetic Engineering of Animal RNA Viruses", Trends in Microbiology, 4(10), (1996), 386-393.

Conzelmann, K,-K., "Genetic manipulation of non-segmented negative-strand RNA viruses", Journal of General Virology, 77(Pt. 3), (Mar. 1996), 381-389.

Conzelmann, K.-K., "Nonsegmented Negative-Strand RNA Viruses: Genetics and Manipulation of Viral Genomes", Annu. Rev. Genet., 32, (1998), 123-162.

Conzelmann, K.-K., "Rescue of Synthetic Genomic RNA Analogs of Rabies Virus by Plasmid-Encoded Proteins", Journal of Virology, 68(2), (1994), 713-719.

De, B. P., et al., "Requirements and Functions of Vesicular Stomatitis Virus L and NS Proteins in the Transcription Process in Vitro", Biochemical and Biophysical Research Communications, 126(1), (1985), 40-49.

De, B. P., et al., "Rescue of synthetic analogues of genome RNA of human parainfluenza virus type 3", Virology, 196(1), (Sep. 1993), 344-348.

De, B. P., et al., "Reverse Genetics of Negative Strand RNA Viruses", Indian Journal of Biochemistry & Biophysics, 31, (1994), 367-375.

De Filette, Marina, et al., "An influenza A vaccine based on tetrameric ectodomain of matrix protein 2", J Biol Chem. 2008 ; 283 (17):, (Feb. 5, 2008), 11382-7.

De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

De La Luna, S., et al., "Influenza Virus NS1 Protein Enhances the Rate of Translation Initiation of Viral mRNAs", Journal of Virology, 69(4), (1995), 2427-2435.

(56) References Cited

OTHER PUBLICATIONS

Desheva, J. A, et al., "Characterization of an influenza A H5N2 reassortant as a candidate for live-attenuated and inactivated vaccines against highly pathogenic H5N1 viruses with pandemic potential", Vaccine, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dreher, T. W., et al., "Mutational Analysis of the Sequence and Structural Requirements in Brome Mosaic Virus RNA for Minus Strand Promoter Activity", Journal of Molecular Biology, (1988), 31-40.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain Of Influenza A M2 Protein Forms Amantadine-Sensitive Proton Channels in Planar Lipid Bilayers", Vilology, 190(1), (Sep. 1992), pp. 485-489.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P., et al., "Recovery of infectious human parainfluenza virus type 3 from cDNA", Virology, 235(2), (Sep. 1, 1997), 323-332.
Elhefnawi, M, et al., "Identification of novel conserved functional motifs across most Influenza A viral strains", Viral J. Jan. 27, 2011;8:44. doi: 10.1186/1743-422X-8-44, (2011), 2 pgs.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Fischer, W. B, et al., "Viral ion channels: structure and function.", Biochim Biophys Acta., 1561(1), (Mar. 19, 2002), 27-45.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012).
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.

Garcia-Sastre, A., et al., "Genetic Manipulation of Negative-Strand RNA Virus Genomes", Annu. Rev. Microbiol., 47, (1993), 765-790.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Giddings, A M, et al., "The matrix protein of HIV-1 is not sufficient for assembly and release of virus-like particles", Virology, 248(1), (1998), 108-16.
Gorman, O T, "Evolution of influenza A virus PB2 genes: implications for evolution of the ribonucleoprotein complex and origin of human influenza A virus", Department of Virology and Molecular Biology, St. Jude Children's Research Hospital, Memphis Tennessee 38101-0318 J. Virol. Oct. 1990; 64(10):4893-902, (1990), 2 pgs.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Grambas, S., et al., "Influence of amantadine resistance mutations on the pH reauiatory function of the M2 protein of influenza A viruses", Virology, 191(2), (Dec. 1992), 541-549.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Hai, Bong, et al., "Influenza B Virus NS1-Truncated Mutants: Live-Attenuated Vaccine Approach", Journal of Virology, 82(21), (2008), 10580-10590.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza a Virus NS1 Protein to dsRNA in vitro", Journal of General Virology, 73, (1992), 3325-3329.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Holsinger, L. J., et al., "Influenza A Virus M2 Ion Channel Protein: a Structure-Function Analysis", Journal of Virology, 68 (3), (1994), pp. 1551-1563.

(56) References Cited

OTHER PUBLICATIONS

Horimoto, T., et al., "Enhanced growth of seed viruses for H5N1 influenza vaccines", Virology, 366(1), (Sep. 15, 2007), 23-27.

Horimoto, T., et al., "Generation of Influenza A Viruses with Chimeric (Type A/B) Hemagglutinins", Journal of Virology, 77(14), (2003), 8031-8038.

Horimoto, T., et al., "The Development and Characterization of H5 Influenza Virus Vaccines Derived from a 2003 Human Isolate", Vaccine, 24(17), (2006), 3669-3676.

Huang, T.-S., et al., "Determination of Influenza Virus Proteins Required for Genome Replication", Journal of Virology, 64(11), (1990), 5669-5673.

Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.

Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.

Iwatsuki-Horimoto, K., et al., "The cytoplasmic tail of the influenza A virus M2 protein plays a role in viral assembly.", J Virol 80(11), (Jun. 2006), 5233-40.

Jackson, D., et al., "A reverse genetics approach for recovery of recombinant influenza B viruses entirely from cDNA.", J Virol., 76(22), (Nov. 2002), 11744-7.

Jang, S.-W., et al., "Deoxygedunin, a Natural Product with Potent Neurotrophic Activity in Mice", PLoS ONE 5(7): e11528, (2010), 1-15.

Jasenosky, Luke D, et al., "Ebola Virus VP40-Induced Particle Formation and Association with the Lipid Bilayer", Journal of Virology, 75 (110, (Jun. 2001), 5205-5214.

Kaplan, G., et al., "In vitro Synthesis of Infectious Poliovirus RNA", Proc, Natl. Acad. Sci. USA, 82, (1985), 8824-8428.

Katinger, D., et al., "Attenuated Influenza Viruses as a Vector for Mucosal Immunization Against HIV-1", Vaccines, 97, Cold Spring Harbor, (1997), 315-319.

Kato, A., et al., "Initiation of Sendai Virus Multiplication From Transfected cDNA or RNA With Negative or Positive Sense", Genes to Cells, 1, (1996), 569-579.

Kawaoka, Y, et al., "Sequence requirements for cleavage activation of influenza virus hemagglutinin expressed in mammalian cells", Proc Natl Acad Sci., 85(2), (1988), 324-328.

Kawaoka, Y., "Mutant Cells With Altered Sialic Acid", U.S. Appl. No. 11/644,179, filed Dec. 22, 2006, 51 pgs.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.

Kistner, Otfried, et al., "Cell culture (Vero) derived whole virus (H5N1) vaccine based on wild-type virus strain induces cross-protective immune responses", Vaccine, 25(32), (2007), 6028-6036.

Kobayashi, M., et al., "Reconstitution of Influenza Virus RNA Polymerase From Three Subunits Expressed Using Recombinant Baculovirus System", Virus Research, 22, (1992), 235-245.

Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.

Konarska, M. M., et al., "Structure of RNAs Replicated by the DNA-Dependent T7 RNA Polymerase", Cell, 63(2), (1990), 609-618.

Kovacova, A., et al., "Sequence similarities and evolutionary relationships of influenza virus A hemagglutinins.", Virus Genes, 24(1), (2002), 57-63.

Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.

Kunkel, T. A., "Rapid and Efficient Site-Specific Mutagenesis Without Phenotypic Selection", Proc. Natl. Acad. Sci. USA, 82, (1985), 488-492.

Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.

Lawson, N. D., "Recombinant Vesicular Stomatitis Viruses From DNA", Proc. Natl. Acad. Sci. USA, 92(10), (1995), 4477-4481.

Lazarovits, Janette, et al., "Endocytosis of Chimeric Influenza Virus Hemagulutinin Proteins That Lack a Cytoplasmic Recognition Feature for Coated Pits", The Journal of Cell Biology, vol. 134, No. 2, (1996), 339-348.

Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.

Lee, Dong-Hun, et al., "Progress and hurdles in development of influenza virus-like particle vaccines for veterinary use", Korean Vaccine Society, (2014), 133-139.

Lee, M. S, et al., "Genetic and pathogenic characterization of H6NI avian influenza viruses isolated in Taiwan between 1972 and 2005", Avian Diseases, 50(4), (Dec. 2006), 561-571.

Levis, R., et al., "Deletion Mapping of Sindbis Virus DI RNAs Derived From cDNAs Defines the Sequences Essential for Replication and Packaging", Cell, 44, (1986), 137-145.

Li, K. S, et al., "Genesis of a highly pathogenic and potentially pandemic H5NI influenza virus in eastern Asia", Nature, 430(6996), (Jul. 8, 2004), 209-213.

Li, Y, et al., "Viral liposomes released from insect cells infected with recombinant baculovirus expressing the matrix protein of vesicular stomatitis virus", Journal of Virology, 67 (7), (1993), 4415-4420.

Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.

Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.

Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.

Luytjes, W., "Amplification, Expression, and Packaging of a Foreign Gene by Influenza Virus", Cell, 59(6), (1989), 1107-1113.

Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.

Matsuoka, et al., "Neuraminidase Stalk Length and Additional Glycosylation of the Hemagglutinin Influence the Virulence of Influenza H5N1 Viruses for Mice", Journal of Virology, vol. 83, No. 9 (2009), pp. 4704-4708.

McCown, M F, et al., "The influenza A virus M2 cytoplasmic tail is required for infectious virus production and efficient genome packaging.", J Virol., 79(6), (Mar. 2005), 3595-605.

McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.

McKimm, J. L., et al., "Mutations in a Conserved Residue in the Influenza Virus Neurarninidase Active Site Decreases Sensitivity to Neu5Ac2en-Derived Inhibitors", Journal Virology, 72(3), (1998), 2456-2462.

(56) References Cited

OTHER PUBLICATIONS

Mebatsion, Teshome, et al., "Budding of Rabies Virus Particles in the Absence of the Spike Glycoprotein", Cell, 84(6), (1996), 941-951.

Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.

Mena, I., "Rescue of a Synthetic Choramphenicol Acetyltransferase RNA into influenza Virus-Like Particles obtained from recombinant plasmids", Journal of Virology, 70(8), (1996), 5016-5024.

Mena, I., et al., "Synthesis of Biologically Active Influenza Virus Core Proteins Using a Vaccinia Virus-T7 RNA Polymerase Expression System", Journal of General Virology, 75, (1994), 2109-2114.

Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.

Monto, Arnold S, et al., "Comparative efficacy of inactivated and live attenuated influenza vaccines.", N Engl J Med., 361(13), (Sep. 24, 2009), 1260-7.

Moyer, S. A., et al., "Assembly and Transcription of Synthetic Vesicular Stomatitis Virus Nucleocapsids", Journal of Virology, 65(5), (1991), 2170-2178.

Murakami, Shin, et al,, "Growth Determinants for H5N1 Influenza Vaccine Seed Viruses in MDCK Cells", Journal of Virology, vol. 82, No. 21, (Nov. 2008), 10502-10509.

Murphy, Brian R, et al., "Virulence of Avian Influenza A Viruses for Squirrel Monkeys", Infection and Immunity 37 (3), (Sep. 1982), 1119-1126.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Naito, S., et al., "Function and Structure of RNA Polymerase From Vesicular Stomatitis Virus", The Journal of Biological Chemistry, 251(14), (1976), 4307-4314.

Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.

Neirynck, S., "A universal influenza A vaccine based on the extracellular domain of the M2 protein", Nature Medicine, 5 (10), (Oct. 1999), pp. 1157-1163.

Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.

Neumann, G., et al., "An Improved Reverse Genetics System for Influenza A Virus Generation and Its Implications for Vaccine Production", Proc. Natl. Acad. Sci. USA, 102(46), (2005), 16825-16829.

Neumann, G., et al., "Emergence and pandemic potential of swine-origin H1N1 influenza virus", Nature (London), 459(7249), (Jun. 2009), 931-939.

Neumann, G., et al., "Generation of influenza A virus from cloned cDNAs—historical perspective and outlook for the new millenium.", Rev Med Virol., 12(1), XP002314285, (Jan.-Feb. 2002), 13-30.

Neumann, G., et al., "Generation of influenza A viruses entirely from cloned cDNAs", Proc. Natl. Acad. Sci. USA., 96(16), (1999), 9345-9350.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/, (Jan. 2000), 547-551.

Neumann, G., et al., "Reverse Genetics of Influenza Viruses—Applications in Research and Vaccine Design", Monographs in Virology, 27, (2008), 118-133.

Neumann, G., et al., "RNA Polymerase I-Mediated Expression of Influenza Viral RNA Molecules", Virology, 202(1), (1994), 477-479.

Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

Odagiri, T., et al., "Nucleotide Sequence of the PA Gene of Influenza A/WSN/33 (H1N1)", Nucleic Acids Research, 18 (3), Department of Virology, (Jan. 9, 1990).

Orkin, S. H, et al,, "Report and Recommendations of the Panel to Assess the NIH Investment in Research on Gene Therapy", http://www.nih.gov/news/panelrep.html, (Dec. 7, 1995), 37 pgs.

Palese, P., et al., "47. Orthomyxoviridae: The Viruses and Their Replication", In: Fields Virology (5th Edition), (2007), 90 pgs.

Palese, P., "Negative-Strand RNA Viruses: Genetic Engineering and Applications", Proc. Natl. Acad. Sci. USA, 93(21), (1996), 11354-11358.

Park, Eun K., et al., "The M2 Ectodomain is important for its incorporation into influenza A virions", J. of Virology, vol. 72, No. 3, XP002196797, (Mar. 1998), 2449-2455.

Park, K. H., et al., "Rescue of a Foreign Gene by Sendai Virus", Proc. Natl. Acad. Sci. USA, 88, (1991), 5537-5541.

Pattnaik, A. K., et al., "Cells That Express All Five Proteins of Vesicular Stomatitis Virus From Cloned cDNAs Support Replication, Assembly, and Budding of Defective Interfering Particles", Proc. Nati. Acad. Sci. USA, 88(4), (1991), 1379-1383.

Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.

Pekosz, A., "Commentary—Reverse Genetics of Negative-Strand RNA Viruses: Closing the Circle", Proc. Nati. Acad. Sci. USA, 96, (1999), 8804-8806.

Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

Percy, N., et al., "Expression of a Foreign Protein by Influenza A Virus", Journal of Virology, 68(7), (1994), 4486-4492.

Piller, S C., et al., "Vpr protein of human immunodeficiency virus type 1 forms cation-selective channels in planar lipid bilayers", PNAS, 93, (1996), 111-1115.

Pinto, L. H., et al., "Influenza Virus M2 Protein Has Ion Channel Activity", Cell, 69, (May 1992), pp. 517-528.

Pleschka, S., et al., "A Plasmid-Based Reverse Genetics System for Influenza A Virus", Journal of Virology, 70(6), (1996), 4188-4192.

Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.

Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.

Racaniello, V. R., et al., "Cloned Poliovirus Complimentary DNA Is Infectious in Mammalian Cells", Science, 214, (1981).

Radecke, F., et al., "Rescue of Measles Viruses From Cloned DNA", The EMBO Journal, 14(23), (1995), 5773-5784.

Radecke, F., et al., "Reverse Genetics Meets the Nonsegmented Negative-Strand RNA Viruses", Reviews in Medical Virology, 7, (1997), 49-63.

Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.

Roberts, A., et al., "Minireview—Recovery of Negative-Strand RNA Viruses From Plasmid DNAs: A Positive Approach Revitalizes a Negative Field", Virology, 247(1), (1998), 1-6.

Romanova, J., et al., "Live cold-adapted influenza A vaccine produced in Vero cell line", Virus Research, 103, (2004), 187-193.

Rose, J. K., "Positive Strands to the Rescue Again: A Segmented Negative-Strand RNA Virus Derived From Cloned cDNAs", Proc. Natl. Acad. Sci. USA, 94, (1996), 14998-15000.

(56) References Cited

OTHER PUBLICATIONS

Ruigrok, R W, et al., "Characterization of three highly purified influenza virus strains by electron microscopy", J Gen Virol 65 ( Pt 4), (Apr. 1984), 799-802.
Ruigrok, R W, et al., "Structural Characterization and Membrane Binding Properties of the Matrix Protein VP40 of Ebola Virus", Journal of Molecular Biology, 300(1), 2000), 103-112.
Sansom, M. S., et al., "Influenza virus M2 Protein: a molecular modelling study of the ion channel", Protein Engineering, 6 (1), (1993), pp. 65-74.
Schickli, J. H, et al., "Plasmid-only Rescue of Influenza A Virus Vaccine Candidates", Philosophical Transactions of the Royal Society of London, Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Schotsaert, M, et al., "Universal M2 ectodomain-based influenza A vaccines: preclinical and clinical developments", Expert Rev Vaccines. Apr. 2009;8(4):, 499-508.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Skehel, J. J., et al., "On the Mechanism of Inhibition of Influenza Virus Replication by Amantadine Hydrochloride", The Journal of General Virology, 38 (1), (1977), pp. 97-110.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Takeda, M., et al., "Influenza a virus M2 ion channel activity is essential for efficient replication in tissue culture.", J Virol., 76(3), (Feb. 2002), 1391-9.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Tobler, K, "Effect of cytoplasmic tail truncations on tile activity of the M(2) ion channel of influenza A virus", J Virol., (1999), 9695-701.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Verma, I. M, et al., "Gene Therapy—Promises, Problems and Prospects", Nature, 389, (1997), 239-242.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Watanabe, et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, S., et al., "Influenza A Virus Lacking M2 Protein as a Live Attenuated Vaccine", Journal of Virology, 83(11), (2009), 5947-5950.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, Tokiko, et al., "Influenza A Virus Can Undergo Multiple Cycles of Replication without M2 Ion Channel Activity", Journal of Virology 75(12), (2001), 5656-5662.
Whelan, S. P. J., et al, "Efficient Recovery of Infectious Vesicular Stomatitis Virus Entirely from cDNA Clones", Proc. Natl. Acad. Sci. USA, 92, (1995), 8388-8392.
Williams, Mark A., et al., "Effect of Mutations and Deletions in a Bicistronic mRNA on the Synthesis of Influenza B Virus NB and NA Glycoproteins", Journal of Virology, 63(1), (1989), 8-35.
Wilson, Julie A, et al., "Epitopes Involved in Antibody-Mediated Protection from Ebola Virus", Science, 287, (Mar. 2000), 1664-1666.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Rui, et al., "A live bivalent influenza vaccine based on a H9N2 virus strain", Vaccine, 28, (2010), 673-680.
Xu, X., et al., "Reassortment and evolution of current human influenza A and B viruses", Virus Research, 103, (2004), 55-60.

(56) References Cited

OTHER PUBLICATIONS

Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.

Yannarell, Dean A., et al., "Factors affecting the yield of cold-adapted influenza virus vaccine", Journal of Virological Methods, vol. 64, 161-169, (1997), 1 pg.

Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.

Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.

Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Nat. Acad. Sci. USA, 88, (1991), 5645-5649.

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zobel, A., et al., "RNA Polymerase I Catalysed Transcription of Insert Viral cDNA", Nucleic Acids Research, 21(16), (1993), 3607-3614.

"U.S. Appl. No. 15/593,039, PTO Response to Rule312 Communication dated Oct. 9, 2018", 2 pgs.

* cited by examiner

|  | No. of survivors/No. of tested [a] | |
|---|---|---|
|  | Challenge virus | |
| Vaccine | VN1203 | Indonesia 7 |
| M2del11-HAavir  100 PFU | 8/8 | 8/8 |
| 1000 PFU | 8/8 | 8/8 |
| PBS | 0/8 | 0/8 |

Fig. 6

VACCINES COMPRISING MUTANT ATTENUATED INFLUENZA VIRUSES

CROSS-REFERENCE TO RELATED APPLICATIONS

This application is a continuation of U.S. patent application Ser. No. 13/070,110, filed Mar. 23, 2011, which claims the benefit of the filing date of U.S. Application Ser. No. 61/316,564, filed on Mar. 23, 2010, the disclosures of which are incorporated by reference herein.

STATEMENT OF GOVERNMENT RIGHTS

This invention was made with government support under A1047446 awarded by the National Institutes of Health. The government has certain rights in the invention.

BACKGROUND

Influenza A viruses cause a highly contagious, acute respiratory disease responsible for human suffering and economic burden every winter. Vaccination is a primary means for prophylaxis against influenza infection, and inactivated and live attenuated influenza virus vaccines are currently available. Inactivated vaccines, administered parenterally, are generally 70% to 90% effective for reducing the incidence of clinical illness in healthy persons as long as the antigenicities of the circulating virus strains match those of the vaccine (Cox et al., 1999). However, because mucosal immunity and cytotoxic T-cell responses are limited, protective efficacy of inactivated vaccines lasts for only a short period, requiring annual vaccination. In contrast, live attenuated influenza virus vaccines are intranasally administered and elicit robust mucosal immunity and cellular responses; their protective efficacy, therefore, lasts for longer periods (Cox et al., 2004). Only two live attenuated vaccines are currently on the market, and use of these vaccines in the United States is limited to persons aged 2 to 49 years (CDC, 2007).

Generally, influenza vaccines have been prepared from live, attenuated virus or killed virus which can grow to high titers. Live virus vaccines activate all phases of the immune system and stimulate an immune response to each of the protective antigens, which obviates difficulties in the selective destruction of protective antigens that may occur during preparation of inactivated vaccines. In addition, the immunity produced by live virus vaccines is generally more durable, more effective, and more cross-reactive than that induced by inactivated vaccines. Further, live virus vaccines are less costly to produce than inactivated virus vaccines. However, the mutations in attenuated virus are often ill-defined. For the existing seasonal human influenza, both inactivated virus vaccine and live attenuated virus vaccine are available. In April 2007, the U.S. Food and Drug Administration (FDA) announced the first approval of an inactivated vaccine for humans against the H5N1 virus. However, the available data indicate that inactivated H5 influenza vaccines are suboptimal in their immunogenicity, and a large amount of hemagglutinin (HA) glycoprotein or coadministration of an adjuvant is required to achieve an adequate immune response (Bressen et al., 2006; Lin et al., 2006; Nicholson et al.; 2005; Stephenson et al., 2003; Treanor et al.; 2006).

SUMMARY OF THE INVENTION

The wild-type influenza A virus M2 protein consists of three structural domains: a 24-amino-acid extracellular domain, a 19-amino-acid transmembrane domain, and a 54-amino-acid cytoplasmic tail domain (Lamb et al., 1985; Zebedee et al., 1985). The M2 transmembrane domain has ion channel activity, which functions at an early stage of the viral life cycle between the steps of virus penetration and uncoating (Helenius, 1992; Pinto et al., 1992). The M2 cytoplasmic tail domain has an important role in viral assembly and morphogenesis (Iwatsuki-Horimoto et al., 2006; McCown et al., 2006; McCown et al., 2005). The M2 protein is encoded by a gene segment (the M gene segment) that also encodes the M1 protein, which forms a viral core having viral ribonucleic acid-nucleoprotein complexes. M1 protein and M2 protein share N-terminal sequences. The M2 protein is encoded by a spliced transcript and RNAs encoding the M1 protein and the M2 protein share 3' sequences, although the coding sequences for M1 and M2 in those 3' sequences are in different reading frames. The C-terminal residues of M1 and C-terminal portion of the extracellular domain of M2 are encoded by the overlapping 3' coding sequences.

The invention provides a vaccine comprising an effective amount of an isolated recombinant influenza virus comprising a mutant M gene segment that is mutated so that upon viral replication, the mutant M gene expresses a functional M1 protein and a mutant M2 protein with a deletion of the cytoplasmic tail and a deletion of at least a portion of the transmembrane domain, e.g., internal or C-terminal deletions, and/or includes one or more substitutions in the transmembrane domain. In one embodiment, the mutant M2 protein has a deletion that includes the entire cytoplasmic tail and transmembrane domain of M2, and has one or more residues of the extracellular domain, e.g., has the first 9 to 15 residues of the extracellular domain. The replication of the recombinant virus is attenuated in vivo relative to a corresponding virus without a mutant M gene segment. The recombinant influenza virus of the invention replicates in vitro in the presence of M2 supplied in trans, e.g., producing titers that are substantially the same or at most 10, 100 or 1,000 fold less than a corresponding wild-type influenza virus.

A "functional" M1 protein provides for export of viral nucleic acid from the host cell nucleus, a viral coat, and/or virus assembly and budding. Thus, the M1 protein in the recombinant influenza viruses of the invention has substantially the same function (e.g., at least 10%, 20%, 50% or greater) as a wild-type M1 protein. Thus, any alteration in the M1 coding region in a mutant M gene segment in a recombinant influenza virus does not substantially alter the replication of that virus, e.g., in vitro, for instance, viral titers are not reduced more than about 1 to 2 logs in a host cell that supplies M2 in trans.

As described hereinbelow, an influenza virus with a M gene segment encoding a M2 protein having a deletion of the transmembrane and cytoplasmic domains was prepared in a cell line than expresses M2 in trans. The resulting virus (a M2 "knockout") was infectious, which was surprising as M2 was believed to be critical for the viral life cycle. In addition, the recombinant viruses of the invention unexpectedly produced progeny viruses, e.g., about $10^2$ pfu/mL in cells that did not provide M2 in trans. The virus of the invention is safer than other attenuated viruses because its reversion rate would be expected to be low and it is highly attenuated, as shown by reduced replication in lung and undetectable replication in nasal turbinates (the virus has greatly reduced capacity to replicate in "normal" cells). Moreover, it was surprising that the cytoplasmic tail of M2 was not necessary in vivo and that such a highly attenuated virus was so immunogenic, e.g., provided protective efficacy.

In one embodiment, the live attenuated influenza virus of the invention elicits both systemic and mucosal immunity at the primary portal of infection. In one embodiment, the live, attenuated influenza virus of the invention has reduced replication in lung compared to wild-type influenza virus, e.g., the live, attenuated influenza virus has titers in lung that are at least one to two logs less, and in one embodiment, replication in nasal turbinates is not detectable. The live, attenuated virus may be employed in a vaccine or immunogenic composition, and so is useful to immunize a vertebrate, e.g., an avian or a mammal, or induce an immune response in a vertebrate, respectively.

In one embodiment, the mutations in the M2 gene result in a mutant M2 protein with a deletion of the entire cytoplasmic tail and deletion or substitution of one or more residues in the transmembrane (TM) domain of M2 and may also comprise at least one amino acid substitution in the extracellular domain, or a combination thereof, relative to a corresponding wild-type M2 protein encoded by a M gene segment. For example, substitutions in the TM domain may include those at residues 25 to 43 of M2, e.g., positions 27, 30, 31, 34, 38, and/or 41 of the TM domain of M2. Substitutions and/or deletions in the TM domain may result in a truncated M2 protein that is not embedded in the viral envelope. For example, a deletion of 10 residues at the C-terminus of the transmembrane domain may result in a truncated M2 protein that is not embedded in the viral envelope. In another embodiment of the invention, the mutant M2 protein may also comprise a deletion in at least a portion of the extracellular domain in addition to deletion of the cytoplasmic domain and a deletion in the TM domain. In one embodiment, the mutant M2 protein has a deletion of the entire cytoplasmic tail and the TM domain and at least one residue of the extracellular domain, e.g., 1 to 15 residues, or any integer in between, of the C-terminal portion of the extracellular domain. In yet another embodiment of the invention, the mutant M2 protein having at least a portion of the extracellular domain further comprises a heterologous protein, e.g., the cytoplasmic and/or TM domain of a heterologous protein (a non-influenza viral protein), which may have a detectable phenotype, that is fused to the C-terminus of at least the extracellular domain of M2, forming a chimeric protein. In one embodiment, the presence of one or more substitutions, deletions, or insertions of heterologous sequences, or any combination thereof, in the M2 gene does not substantially alter the properties of the recombinant influenza virus of the invention, e.g., the presence of one or more substitutions, deletions, or insertions of heterologous sequences does not result in virus titers in vitro that are more than about 1.5 to 2 logs lower, and/or does not result in virus that is substantially less attenuated in vivo, than the recombinant influenza virus of the invention with a mutant M2 protein gene having a deletion of the cytoplasmic tail and TM domain of M2.

In one embodiment, the deletion in the TM domain of M2 includes 1, 2, 3, 4, 5 or more, e.g., 11, 12, 13, 14, or 15 residues, up to 19 residues. In one embodiment, the deletion is from 2 up to 9 residues, including any integer in between. In one embodiment, the deletion is from 15 up to 19 residues, including any integer in between. In one embodiment, the deletion is from 10 up to 19 residues, including any integer in between. In one embodiment, the deletion is the result of at least one substitution of a codon for an amino acid to a stop codon. In one embodiment, the deletion is the result of deletion of at least one codon for an amino acid. In one embodiment, the TM domain of M2 has one or more substitutions, e.g., includes 1, 2, 3, 4, 5 or more, e.g., 11, 12, 13, 14, or 15 substitutions, up to 19 residues of the TM domain. In one embodiment, the one or more amino acid deletions and/or substitutions in the TM domain in a mutant M2 protein that also lacks the cytoplasmic tail of M2, provides for a mutant M2 protein that lacks M2 activity and/or when expressed in a virus yields a live, attenuated virus.

In one embodiment, a deletion in the extracellular (ectodomain) domain of M2 may include 1, 2, 3, 4 or more, e.g., 5, 10, 15, or 20 residues, up to 24 residues of the extracellular domain. In one embodiment, the deletion in the extracellular domain is from 1 up to 15 residues, including any integer in between. In one embodiment, the deletion is the result of at least one substitution of a codon for an amino acid to a stop codon. In one embodiment, the deletion is the result of deletion of at least codon for an amino acid. In one embodiment, the extracellular domain of M2 may also include one or more substitutions. In one embodiment, the mutations in the M2 gene of a M gene segment that result in deletion(s) or substitution(s) in the extracellular domain of M2 do not substantially alter the function of the protein encoded by the M1 gene.

In one embodiment of the invention, fewer than 20%, e.g., 10% or 5%, of the residues in the TM domain or extracellular domain are substituted. In one embodiment, fewer than 60%, e.g., 50%, 40%, 30%, 20%, 10%, or 5% of the residues in the extracellular domain are deleted. In one embodiment, more than 20%, 30%, 40%, 50%, 80% or more, of the residues in the TM domain are deleted.

Also provided is a method of preparing a recombinant influenza virus comprising a mutant so that upon viral replication the mutant M gene expresses a functional M1 protein and a mutant M2 protein with a deletion of the cytoplasmic tail and lacking a TM domain or having a imitated TM domain that is truncated and/or includes one or more substitutions, wherein the replication of the recombinant virus is attenuated in vivo relative to a corresponding virus without a mutant M gene. In one embodiment, the virus of the invention may be prepared by mutating a M gene segment. For example, the coding region for the C-terminus of the M1 protein may be mutated by substituting a codon for one, or for two or more adjacent amino acids, in the about 15 C-terminal terminal residues, with one or more stop codons which optionally also substitutes a stop codon in the coding region for the extracellular domain of the M2 protein. The method comprises contacting a host cell with a plurality of influenza vectors, including a vector comprising the mutant M2 sequence, so as to yield recombinant virus. For example, the host cell is contacted with vectors for vRNA production including a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a promoter operably linked to an influenza virus NS DNA linked to a transcription termination sequence, wherein the M DNA comprises mutant M2 DNA for a M2 so that upon viral replication the mutant M gene expresses a functional M1 protein and a mutant M2 protein with a deletion of the cytoplasmic tail and lacking a TM domain or having a mutated TM domain that is truncated and/or includes one or more substitutions; and vectors for mRNA (protein) production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, and optionally one or more of a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding a M2 protein, and a vector comprising a promoter operably linked to a DNA segment encoding influenza virus NS. The host cell may stably express M2, or may be induced to stably express M2. In one embodiment, separate vectors for M1 and M2 vRNA, and/or for NS1 and NS2 vRNA, in place of vectors for M vRNA and/or NS vRNA, are provided and employed. In one embodiment, the promoter in a vRNA vector includes but is not limited to a RNA polymerase I (PolI) promoter, e.g., a human RNA PolI promoter, a RNA polymerase II (PolII) promoter, a RNA polymerase III promoter, a SP6 promoter, a T7 promoter, or a T3 promoter. In one embodiment, one or more vRNA vectors include a PolII promoter and ribozyme sequences 5' to influenza virus sequences and the same or different ribozyme sequences 3' to the influenza virus sequences. In one embodiment, the mutant M2 gene is in a vector and is operably linked to a promoter including, but not limited to, a RNA PolI promoter, e.g., a human RNA PolI promoter, a RNA PolII promoter, a RNA polymerase III promoter, a SP6 promoter, a T7 promoter, or a T3 promoter. In one embodiment, the vRNA vectors include a transcription termination sequence including, but not limited to, a PolI transcription termination sequence, a PolII transcription termination sequence, or a PolIII transcription termination sequence, or one or more ribozymes. In one embodiment, the host cell is not contacted with the NA vector, and the resulting virus is further attenuated. In one embodiment, one or more vectors for vRNA production are on the same plasmid (see, e.g., U.S. published application No. 20060166321, the disclosure of which is incorporated by reference herein). In one embodiment, one or more vectors for mRNA production are on the same plasmid (see, e.g., U.S. published application No. 2006/0166321).

In another embodiment, the method includes contacting a host cell with a vector having a PolII promoter linked to a PolI transcription termination sequence linked to an influenza virus PA DNA linked to a PolI promoter linked to a PolIII transcription termination sequence (a bidirectional cassette), a vector having a PolII promoter linked to a PolI transcription termination sequence linked to an influenza virus PB1 DNA linked to a PolI promoter linked to a PolIII transcription termination sequence, a vector having a PolII promoter linked to a PolI transcription termination sequence linked to an influenza virus PB2 DNA linked to a PolI promoter linked to a PolIII transcription termination sequence, a vector having a PolII promoter linked to a PolI transcription termination sequence linked to an influenza virus HA DNA linked to a PolI promoter linked to a PolIII transcription termination sequence, a vector having a PolII promoter linked to a PolI transcription termination sequence linked to an influenza virus NP DNA linked to a PolI promoter linked to a PolIII transcription termination sequence, a vector having a PolII promoter linked to a PolI transcription termination sequence linked to an influenza virus NA DNA linked to a PolI promoter linked to a PolIII transcription termination sequence, a vector having a PolII promoter linked to a PolI transcription termination sequence linked to an influenza virus M DNA linked to a PolI promoter linked to PolIII transcription termination sequence, and a vector having a PolII promoter linked to a PolI transcription termination sequence linked to an influenza virus NS DNA linked to a PolI promoter linked to PolIII transcription termination sequence, wherein the M DNA comprises mutant M2 DNA for a M2 so that upon viral replication the mutant M gene expresses a functional M1 protein and a mutant M2 protein with a deletion of the cytoplasmic tail and lacking a TM domain or having a mutated TM domain that is truncated and/or includes one or more substitutions, wherein the replication of the recombinant virus is attenuated in vivo relative to a corresponding virus without a mutant M gene segment. The host cell may stably express M2, or may be induced to stably express M2.

Also provided is a method of preparing a recombinant influenza virus comprising a mutant M2 gene for a M2 so that upon viral replication the mutant M gene expresses a functional M1 protein and a mutant M2 protein with a deletion of the cytoplasmic tail and lacking a TM domain or having a mutated TM domain that is truncated and/or includes one or more substitutions, wherein the replication of the recombinant virus is attenuated in vivo relative to a corresponding virus without the mutant M gene segment. The method comprises contacting a host cell with a plurality of influenza vectors, including a vector comprising a PolI promoter operably linked to an influenza virus PA DNA linked to a PolI transcription termination sequence, a vector comprising a PolI promoter operably linked to an influenza virus PB1 DNA linked to a PolI transcription termination sequence, a vector comprising a PolI promoter operably linked to an influenza virus PB2 DNA linked to a PolI transcription termination sequence, a vector comprising a PolI promoter operably linked to an influenza virus HA DNA linked to a PolI transcription termination sequence, a vector comprising PolI promoter operably linked to an influenza virus NP DNA linked to a PolI transcription termination sequence, a vector comprising a PolI promoter operably linked to an influenza virus DNA NA linked to a PolI transcription termination sequence, a vector comprising a PolI promoter operably linked to an influenza virus M DNA linked to a PolI transcription termination sequence, and a vector comprising a PolI promoter operably linked to an influenza virus NS DNA linked to a PolI transcription termination sequence. The sequence of the DNA for M comprises a M2 sequence for a mutant M2 so that upon viral replication the mutant M gene expresses a functional M1 protein and a mutant M2 protein with a deletion of the cytoplasmic tail and lacking a TM domain or having a mutated TM domain that is truncated and/or includes one or more substitutions, wherein the replication of the recombinant virus is attenuated in vivo relative to a corresponding virus without the mutant M gene segment; and a vector comprising a PolII promoter operably linked to a DNA segment encoding influenza virus PA, a vector comprising a PolII promoter operably linked to a DNA segment encoding influenza virus PB1, a vector comprising a PolII promoter operably linked to a DNA segment encoding influenza virus PB2, a vector comprising a PolII promoter operably linked to a DNA segment encoding influenza virus NP, and optionally one or more of a vector comprising a PolII promoter operably linked to a DNA segment encoding influenza virus HA, a vector comprising a PolII promoter operably linked to a DNA segment encoding influenza virus NA, a vector comprising a PolII promoter operably linked to a DNA segment encoding influenza vines M and a vector comprising a PolII promoter operably linked to a DNA segment encoding influenza virus NS. The host cell may stably express M2, or may be induced to stably express M2. In one embodiment, separate vectors for M1 and M2 vRNA, and/or for NS1 and NS2 vRNA, in place of vectors for M vRNA and/or NS vRNA, are provided and employed. In one embodiment, the PolI promoter is a human PolI promoter. In one embodiment, the PolI promoter for each PolI containing vector is the same. In one embodiment, the PolII promoter for each PolII containing vector is the same. In one embodiment, the PolII promoter for two or more, but not all, of the PolII containing vectors, is the same. In one embodiment, the PolII promoter for each PolII containing vector is different.

The invention further provides a composition having one or more of the vectors described above, and a host cell contacted with such a composition, e.g., so as to yield infectious virus. The host cell may be contacted with each vector, or a subset of vectors, sequentially. One or more of the vectors may be on plasmids. The compositions and host cells of the invention may also include another vector for vRNA production or protein production that includes heterologous sequences, e.g., for a marker gene, or a therapeutic or prophylactic gene, e.g., an immunogen for a cancer associated antigen or for a pathogen such as a bacteria, a noninfluenza virus, fungus, or other pathogen.

In one embodiment, the recombinant virus of the invention includes one or more genes from influenza A virus. In another embodiment, the recombinant virus of the invention may include one or more genes from influenza B virus, e.g., an influenza B HA gene. In yet another embodiment, the recombinant virus of the invention may include one or more genes from influenza C virus.

In one embodiment, the influenza DNA in a vector is a DNA with a native (naturally occurring) influenza virus sequence. In one embodiment, the influenza DNA is a DNA that has been manipulated in vitro, e.g., by inserting, deleting or substituting, or a combination thereof, one or more nucleotides in, for example, the coding region.

The HA sequences in a recombinant virus of the invention may be any one of the sixteen influenza A HA sequences, a chimeric HA sequence or any non-native HA sequence. The NA sequences in a recombinant virus of the invention may be any one of the nine influenza A NA sequences, a chimeric NA sequence or any non-native NA sequence.

In one embodiment, other attenuating mutations may be introduced to the vectors, e.g., a mutation in a HA cleavage site that results in a site that is not cleaved.

Further provided is a receptacle containing a composition comprising one or more influenza viruses, at least one of which is a live, attenuated influenza virus of the invention, each in an amount effective to provide a protective immune response. In one embodiment, the composition is formulated for intranasal delivery.

BRIEF DESCRIPTION OF THE FIGURES

FIGS. 4A-4C. Virus-specific serum and mucosal antibody responses in mice immunized with the M2del11-HAavir virus. Mice were immunized with 100 or 1,000 PFU of M2del11-HAavir virus intranasally. Samples from each group were obtained 3 weeks postimmunization. IgG and IgA levels in sera (A), lung washes (B), and nasal washes (C) from individual mice were detected by ELISA. Values are expressed as the mean absorbance±standard deviation (n=4) of undiluted samples (trachea-lung and nasal washes) or of samples diluted 1:10 (sera). Differences between responses to PBS and the M2del11-HA virus were tested for statistical significance by the use of Student's t test. M2del11-HAavir showed substantial levels of virus-specific IgG titers in serum and lung wash as well as IgA titers in lung wash, which increased with the immunization dose. These data indicate that M2del11-HAavir was able to induce strong antibody responses in mice.

Figure 5:
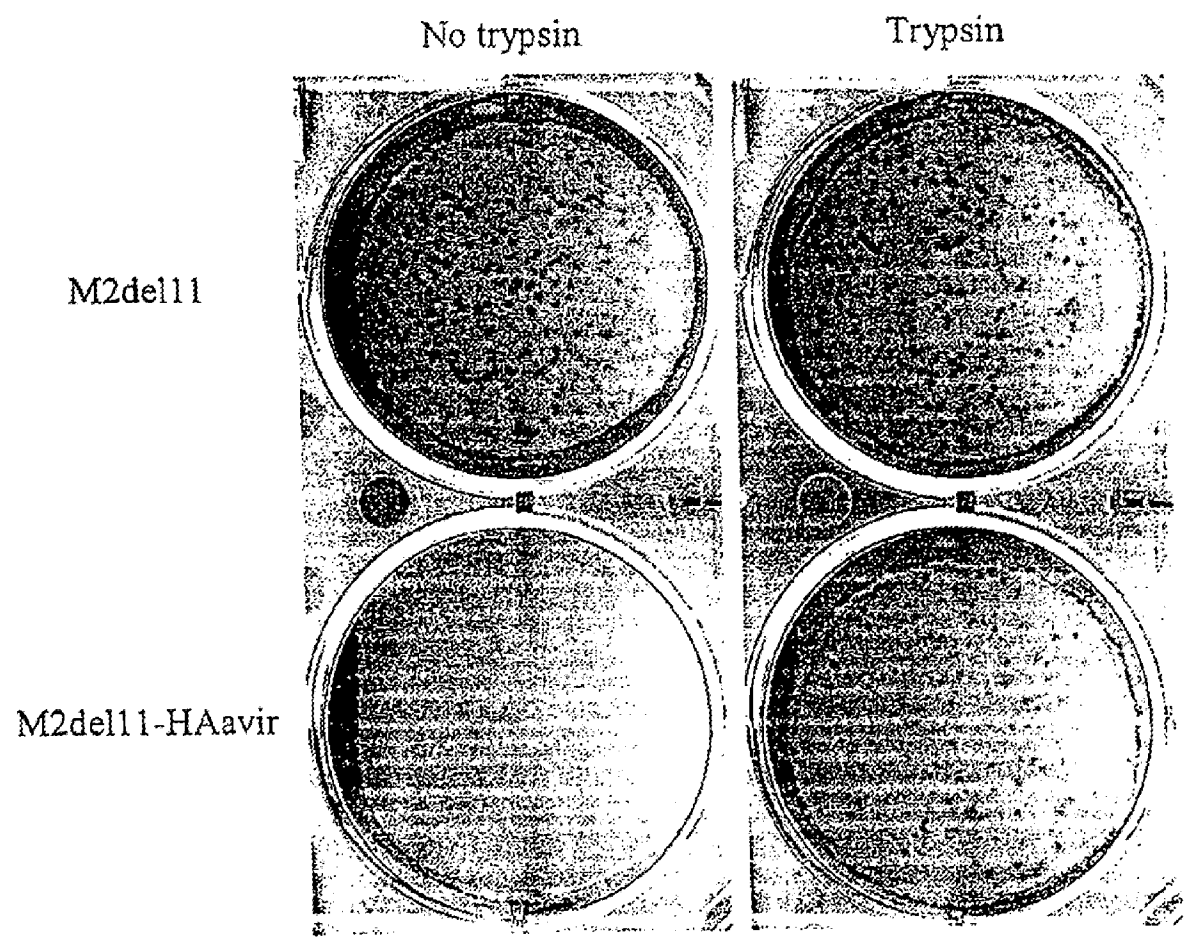

FIG. 5. Trypsin dependence of plaque formation of M2del11-HAavir virus in M2CK cells. Plaque assays were performed on M2CK cells in the presence or absence of trypsin. M2del11 virus was able to form plaques in both the presence and absence of trypsin. In contrast, with M2del11-HAavir mutant virus, clear plaques were visible only in the presence of trypsin.

FIG. 6. Protection against challenge with lethal doses of H5 viruses of mice immunized with M2del11-HAavir virus. One month after immunization of mice with M2del1 1-HA, the immunized mice virus survived a lethal challenge with 100 MLD$_{50}$ of highly pathogenic H5N1 viruses (VN1203 or Indonesia 7 virus) and did not show any symptom (i.e., weight loss) after challenge, whereas all of the control mice died or had to be euthanized due to their disease by day 8 post-challenge.

DETAILED DESCRIPTION OF THE INVENTION

Definitions

Figure 1:
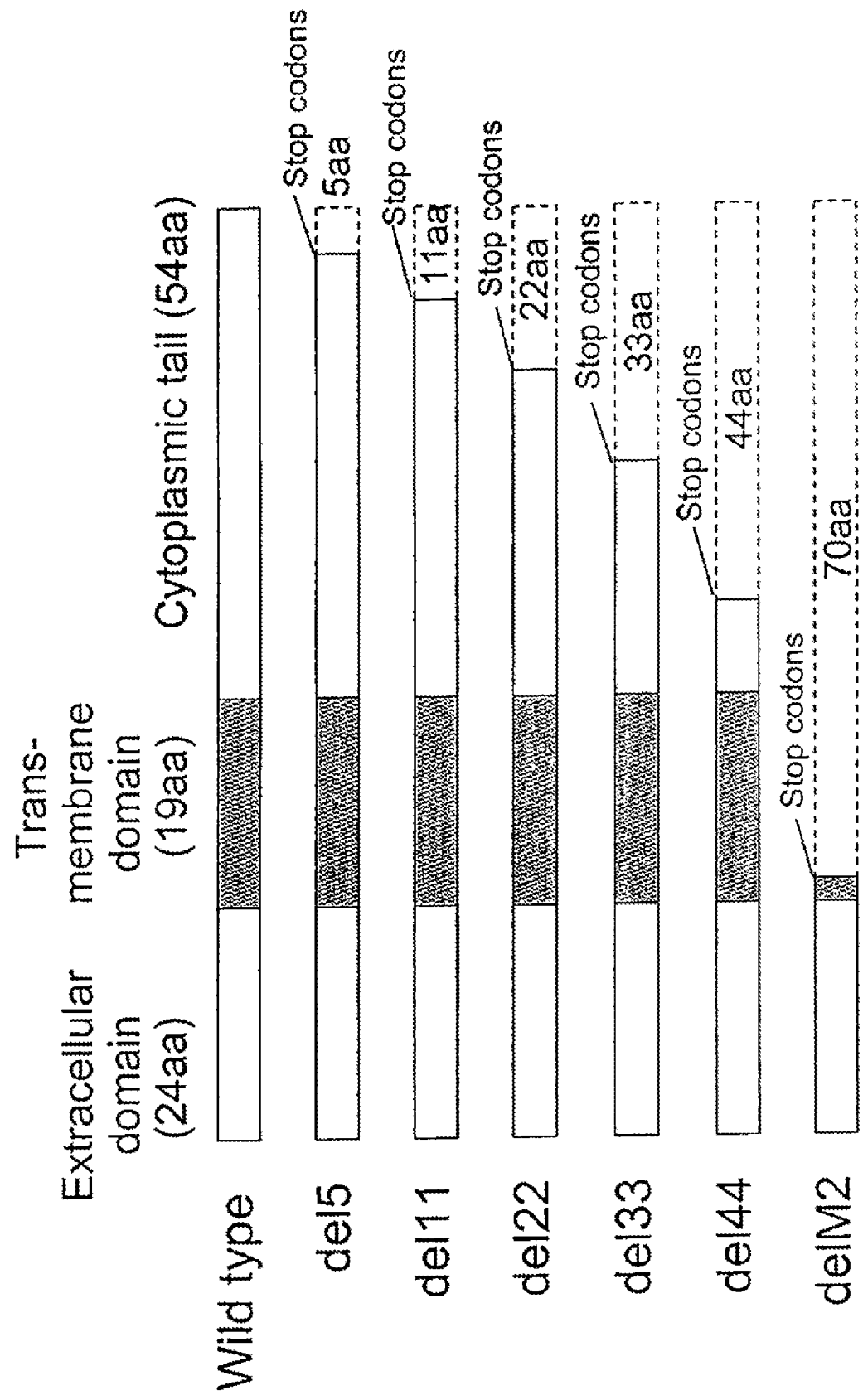
FIG. 1. Schematic representation of M2 mutants. The M gene was derived from a highly pathogenic H5N1 (VN1203) virus. The mutants del5, del11, del22, del33, and del44 contain a 5-, 11-, 22-, 33-, or 44-amino-acid (aa) deletion from the C-terminus, respectively. The mutant delM2 was constructed by deletion of 70 C-terminal residues, including the entire TM and cytoplasmic domains.

As used herein, the terms "isolated and/or purified" refer to in vitro preparation, isolation and/or purification of a nucleic acid molecule such as a vector, plasmid of the invention or a virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome, or otherwise artificially generated.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Influenza Virus

The life cycle of viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell. Different viral proteins play a role in each of these steps.

The influenza A virus is an enveloped negative-strand virus with eight RNA segments encapsidated with nucleoprotein (NP). The eight single-stranded negative-sense viral RNAs (vRNAs) encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase (HEF) rather than individual HA and NA proteins.

Spanning the viral membrane for influenza A virus are three proteins: hemagglutinin (HA), neuraminidase (NA), and M2. The extracellular domains (ectodomains) of HA and NA are quite variable, while the ectodomain domain of M2 is essentially invariant among influenza A viruses. The M2 protein which possesses ion channel activity (Pinto et al., 1992), is thought to function at an early state in the viral life cycle between host cell penetration and uncoating of viral RNA (Martin and Helenius, 1991; reviewed by Helenius, 1992; Sugrue et al., 1990). Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm (reviewed by Helenius, 1992). In addition, among some influenza strains whose HAs are cleaved intracellularly A/fowl plagues/Rostock/34), the M2 ion channel is thought to raise the pH of the trans-Golgi network, preventing conformational changes in the HA due to conditions of low pH in this compartment (Hay et al., 1985; Ohuchi et al., 1994; Takeuchi and Lamb, 1994).

Evidence that the M2 protein of influenza virus has ion channel activity was obtained by expressing the protein in oocytes of Xenoptis laevis and measuring membrane currents (Pinto et al., 1992; Wang et al., 1993; Holsinger et al., 1994). Specific changes in the M2 protein TM domain altered the kinetics and ion selectivity of the channel, providing strong evidence that the M2 TM domain constitutes the pore of the ion channel (Holsinger et al., 1994). In fact, the M2 TM domain itself can function as an ion channel (Duff and Ashley, 1992). M2 protein ion channel activity is thought to be essential in the life cycle of influenza viruses, because amantadine hydrochloride, which blocks M2 ion channel activity (Hay et al., 1993), inhibits viral replication (Kato and Eggers, 1969; Skehel et al., 1978).

Exemplary Viruses and Methods

The invention provides recombinant influenza viruses useful in vivo. In one embodiment, the invention provides an isolated recombinant influenza virus comprising a mutant M2 gene so that upon viral replication the mutant M gene segment expresses a functional M1 protein and a mutant M2 protein with a deletion of the cytoplasmic tail and lacking a TM domain or having a mutated TM domain that is truncated and/or includes one or more substitutions, wherein the replication of the recombinant virus is attenuated in vivo relative to a corresponding virus without a mutant M gene segment, wherein the replication of the virus in vitro in the presence of M2 supplied in trans is not substantially altered but the recombinant virus is attenuated in vivo relative to a corresponding virus without the deletion.

In one embodiment, the M2 protein has a deletion in the TM domain of at least 3 up to 19 residues. In one embodiment, the deletion that includes residues 29 to 31. In one embodiment, the deletion is at least 5 up to 19 residues. In another embodiment, the deletion is at least 15 residues. In yet another embodiment, the deletion is at least 10 residues. In another embodiment, the deletion is at least 10 residues. In a further embodiment, the deletion includes the entire TM domain.

In one embodiment, the mutant M2 protein further comprises a heterologous protein at the C-terminus. In one embodiment, the mutant M2 protein further comprises at least one amino acid substitution, e.g., in the TM domain of the M2 protein. The isolated virus may further include another attenuating mutation(s) in addition to the deleted M2 protein.

In one embodiment, the recombinant virus comprises influenza A HA, for instance, H5 HA. In one embodiment, the HA is not H3 HA.

Also provided is a method of preparing a recombinant influenza vines comprising a mutant M2 protein gene. The method includes contacting a host cell with a plurality of influenza vectors so as to yield recombinant influenza virus. The plurality of vectors includes: vectors for vRNA production including a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a promoter operably linked to an influenza virus NS DNA linked to a transcription termination sequence, wherein the M DNA comprises mutant M2 DNA for a mutant M2 protein with a deletion of the cytoplasmic tail and lacking a TM domain or having a mutated TM domain that is truncated and/or includes one or more substitutions; and b) vectors for protein production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, and a vector comprising a promoter operably linked to a DNA segment encoding influenza virus NS. Virus which replicates in vitro but is attenuated in vivo is isolated from the host cells. In one embodiment, the vector for vRNA production of HA comprises H5 DNA, e.g., one with a mutant cleavage site associated with reduced virulence. In one embodiment, the promoter in the vectors for vRNA production is a PolI promoter. In one embodiment, the vector for vRNA production of HA comprises influenza A HA DNA.

Further provided are compositions with one or more vectors of the invention. In one embodiment, a composition includes a plurality of influenza vectors, for instance, vectors for vRNA production including a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus PB1 DNA linked to a transcription termination sequence, and a vector comprising a promoter operably linked to an influenza virus NS DNA linked to a transcription termination sequence, wherein the M DNA comprises mutant M2 DNA so that upon viral replication the mutant M gene expresses a functional M1 protein and a mutant M2 protein with a deletion of the cytoplasmic tail and lacking a TM domain or having a mutated TM domain that is truncated and/or includes one or more substitutions, wherein the replication of the recombinant virus is attenuated in vivo relative to a corresponding virus without a mutant M gene segment; and vectors for mRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, and a vector comprising a promoter operably linked to a DNA segment encoding influenza virus NS. In one embodiment, the composition further includes a vector comprising a promoter operably linked to a heterologous DNA sequence of interest, e.g., wherein the vector comprises a DNA sequence for an immunogenic polypeptide or peptide of a pathogen or wherein the vector comprises a DNA sequence for a therapeutic protein. In one embodiment, two or more of the vectors for vRNA production are on the same plasmid. In one embodiment, two or more of the vectors for mRNA production are on the same plasmid.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as that commercialized under the name TRITON X100. The hemagglutinin may also be isolated after treatment of the virions with a protease such as bromelin, then purified by a method such as that described by Grand and Skehel.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or p-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are generally employed.

Live Attenuated Virus Vaccines. Live, attenuated influenza virus vaccines, can also be used for preventing or treating influenza virus infection, according to known method steps. Attenuation may be achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the circulating wild-type strains. The attenuated genes are derived from the attenuated parent. In this approach, genes that confer attenuation do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production. Reassortant progeny are then selected at 25° C. (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced, for example, into the PB2 polymerase gene or the NS gene. Thus, new donor viruses can also be generated bearing attenuating mutations introduced by site-directed mutagenesis, and such new donor viruses can be used in the production of live attenuated reassortant H1N1 and H3N2 vaccine candidates in a manner analogous to that described above for the A/AA/6/60 ca donor virus.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, for example, 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are often employed. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. One mode of using a pharmaceutical composition of the present invention is by intramuscular or subcutaneous application.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective closes provided below are not intended to limit the invention and represent exemplary dose ranges. However, the dosage will be tailored to the individual subject, as is understood and determinable by one of skill in the art.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children ☐3 years of age, and 7.5 µg per component for older children <3 years of age. The quantity of NA can also be standardized, however, this glycoprotein can be labile during the processor purification and storage. Each 0.5-ml dose of vaccine may contain approximately 1-50 billion virus particles, and for example 10 billion particles.

The invention will be further described by the following non-limiting examples.

EXAMPLE 1

Materials and Methods

Cells. 293T human embryonic kidney cells and Madin-Darby canine kidney (MDCK) cells were maintained in Dulbecco's modified Eagle's medium supplemented with 10% fetal calf serum and in minimal essential medium (MEM) containing 5% newborn calf serum, respectively. All cells were maintained at 37° C. in 5% $CO_2$. Hygromycin-resistant MDCK cells stably expressing M2 protein from A/Puerto Rico/8/34 (H1N1) were established by cotransfection with plasmid pRHyg, containing the hygromycin resistance gene, and plasmid pCAGGS/M2, expressing the full-length M2 protein, at a ratio of 1:1. The stable MDCK cell clone (M2CK) expressing M2 was selected in medium containing 0.15 mg/mL of hygromycin (Roche, Mannheim, Germany) by screening with indirect immunostaining using an anti-M2 (14C2) monoclonal antibody. The M2CK cells were cultured in MEM supplemented with 10% fetal calf serum and 0.15 mg/mL of hygromycin. In M2CK cells, the expression levels and localization of M2 were similar to those in virus-infected cells (data not shown).

Plasmid construction. The cDNA of A/Vietnam/1203/04 (VN1203) virus was synthesized by reverse transcription of viral RNA with an oligonucleotide complementary to the conserved 3' end of the viral RNA, as described by Katz et al. (1990). The cDNA was amplified by PCR with M gene-specific oligonucleotide primers containing BsmBI sites, and PCR products were cloned into the pGEM vector. The resulting construct was designated pGEM-VN1203M. After digestion with BsmBI, the fragment was cloned into the BsmBI sites of the pHH21 vector, which contains the human RNA polymerase I promoter and the mouse RNA polymerase I terminator, separated by BsmBI sites, resulting in pPolIUdM. Plasmids derived from pHH21 for the expression of viral RNA are referred to as "PolI" constructs herein.

The M mutants were constructed as follows. pGEM-VN1203M was first amplified by inverse PCR (Ochmann et al., 1988) using the back-to-back primers M987stopF (5'-gtgaATAGAATTGGAGTAAAAAACTACC-3'; SEQ ID NO:1) and M987stopR (5'-tcaAAAATGACCATCGTCAA-CATCCAC-3'; SEQ ID NO:2), M969stopF (5'-gtgaGATGGTCATTTTGTCAACATAGAA-3'; SEQ ID NO:3) and M969stopR (5'-tcaATC-CACAGCACTCTGCTGTTCCTG-3'; SEQ ID NO:4), M936stopF (5'-gtgaCGGCAGGAACAGCAGAGTGCTG-3'; SEQ ID NO:5) and M936stopR (5'-tcaTTCCCTCATA-GACTCAGGTACC-3'; SEQ ID NO:6), M903stopF (5'-gtgaGCAGGGGTACCTGAGTCTATG-3;SEQ ID NO:7) and M903stopR (5'-tcaAGGCCCTCTTTTCAAACCGTA-3; SEQ ID NO:8), M870stopF (5'-CTTAAATACGGTTT-GAAAAGAGGGCCTGC-3'; SEQ ID NO:9) and M870stopR (5'-tcactcaATAAATGCATTTGAAGAAAA-GACGATC-3; SEQ ID NO:10), and M783stopF (5'-TTGTTGTTGCCGCAAATATCATTGGG-3; SEQ ID NO:11) and M783stopR(5'-TtcactcaACTTGAATCGCTG-CATCTGC-3'; SEQ ID NO:12). Nucleotide changes to introduce stop codons are indicated by lowercase letters.

The PCR products were then phosphorylated, self-ligated, propagated in *Escherichia coil* strain DH5α, and then digested with BsmBI and cloned into the BsmBI sites of the pHH21 vector. The resulting constructs were designated pPolI-VN1203M2del5, pPolI-VN1203M2del11, pPolI-VN1203M2del22, pPolI-VN1203M2del33, pPolI-VN1203M2del44, and pPolI-VN1203delM2, each of which contained two stop codons at nucleotide positions 972 to 974, 939 to 941, 906 to 908, 873 to 875, and 786 to 788 of the M segment, which resulted in the deletion of 5, 11, 22, 33, 44, and 70 residues from the C-terminus of the M2 protein, respectively (FIG. 1). All of the constructs were sequenced to ensure that unwanted mutations were not present.

Plasmid-driven reverse genetics. All of the viruses were generated by the introduction of plasmids expressing eight viral RNA segments and three polymerase proteins plus NP, as described by Neumann et al. (1999). At 48 hours post-transfection, viruses were harvested and used to inoculate M2CK cells for the production of stock viruses. The M genes of transfectant viruses were sequenced to confirm the origin of the gene and the presence of the intended mutations and to ensure that no unwanted mutations were present. All experiments with live viruses and with transfectants generated by reverse genetics were performed in a biosafety level 3 containment laboratory approved for such use by the CDC and the U.S. Department of Agriculture.

Replicative properties of the transfectant viruses in cell culture. MDCK cells were infected in duplicate wells of 24-well plates with the wild-type or mutant viruses at a multiplicity of infection (MOI) of 0.001, overlaid with MEM containing 0.5 µg of trypsin per mL, and incubated at 37° C. At select time points, supernatants were assayed for infectious virus in plaque assays on M2CK cells (Iwatsuki-Horimoto et al., 2006).

Experimental infection. Five-week-old female BALB/c mice, anesthetized with isoflurane, were infected intranasally with 50 µL (100 PFU) of virus. Virus titers in organs were determined 3 days after infection by use of MDCK cells, as described in Bilsel et al. (1993).

Immunization and protection. BALB/c mice (4-week-old females) were intranasally immunized with 100 or 1,000 PFU/50 µL of the M2del11-HAavir virus. Three weeks later, four mice were sacrificed to obtain sera, trachea-lung washes, and nasal washes. One month after vaccination, immunized mice were challenged intranasally, under anesthesia, with $3.8 \times 10^2$ PFU or $5 \times 10^4$ PFU of the wild-type VN1203 or A/Indonesia/7/05 virus, which was equivalent to 100 50% minimal lethal doses ($MLD_{50}$) (dose required to kill 50% of infected mice), respectively. To determine virus titers in mice, organ samples were harvested at day 3 postchallenge and were homogenized and titrated on MDCK cells. The remaining animals were observed for clinical signs and symptoms of infection for 14 days postchallenge.

Virus-specific antibody detection Immunoglobulin G (IgG) and IgA antibody titers were measured in sera, trachea-lung washes, and nasal washes of the immunized mice by use of an enzyme-linked immunosorbent assay (ELISA) (Kida et al., 1982). In this assay, the wells were coated with purified A/Vietnam/1194/05 virus after treatment with 0.05 M Tris-HCl (pH 7.8) containing 0.5% Triton X-100 and 0.6 M KCl at room temperature for 1 hour and then diluted in phosphate-buffered saline (PBS). After incubation of virus-coated plates with test serum samples for 1 hour, bound antibody was detected with a rabbit anti-mouse IgA (Kirkegaard & Perry Laboratories Inc., Gaithersburg, Md.) and a goat anti-mouse IgG (Boehringer, Mannheim, Germany) conjugated to horseradish peroxidase. Neutralizing antibody titers in serum samples of the immunized mice were also evaluated. The sera were treated with receptor-destroying enzyme (Accurate Chemical and Scientific Corp.) to destroy inhibitors of influenza virus replication. After inactivation of the receptor-destroying enzyme by treatment at 56° C. for 30 minutes, VN1203 and A/Indonesia/7/05 viruses were each incubated with twofold serial dilutions of serum (starting at a 1:10 dilution) at 37° C. for 1 hour. Viral infectivity was determined by titration of the samples in a plaque assay on MDCK cells. The neutralizing titer was defined as the reciprocal titer of serum required to neutralize at least 50% of each virus.

Results

In vitro growth properties of VN1203 viruses possessing M2 cytoplasmic tail deletion mutations. A series of M2 cytoplasmic tail deletion mutants of a highly pathogenic H5N1 (VN1203) virus was generated by reverse genetics as described in Neumann et al. (1999). Transfectant viruses were harvested at 48 hours posttransfection and used to inoculate M2CK cells to propagate stock viruses. The stock virus titers were comparable to that of the wild-type virus: $6.2 \times 10^8$ PFU/mL for VN1203M2del44, $6.8 \times 10^8$ PFU/mL for VN1203M2del33, $6.3 \times 10^8$ PFU/mL for VN1203M2del22, $5.4 \times 10^8$ PFU/mL for VN1203M2dl11, $6.1 \times 10^8$ PFU/mL for VN1203M2del5, and $2.4 \times 10^8$ PFU/mL for the wild-type virus. The only exception was VN1203delM2 ($6.0 \times 10^6$ PFU/mL).

Figure 2:
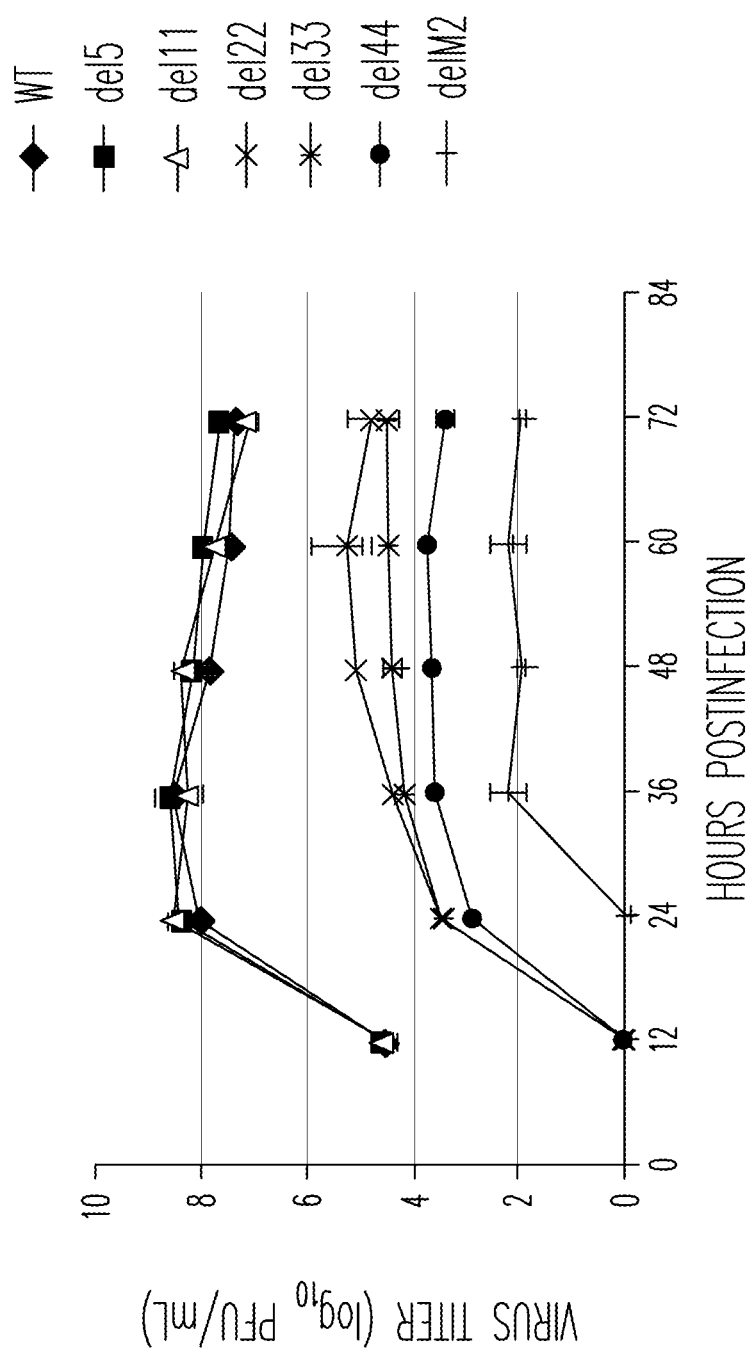
FIG. 2. Growth kinetics of the M2 tail deletion mutant viruses in MDCK cells. MDCK cells were infected with the M2 tail deletion mutant viruses at an MOI of 0.001. At the indicated times after infection, the virus titer in the supernatant was determined with M2CK cells. The values presented are means from duplicate experiments. WT, wild-type. The del5 and del 11 mutants grew as well as the wild-type virus, whereas the del22, del33, del44, and delM2 replicated less efficiently than did the wild-type virus in MDCK cells (about 1,000 to about 10,000-fold lower).

Next, the growth properties of the VN1203 M2 tail mutant viruses were compared with those of wild-type VN1203 virus in MDCK cells (FIG. 2). MDCK cells were infected with viruses at an MOI of 0.001, and their growth kinetics were monitored for 72 hours. The VN1203M2del5 and –M2del11 viruses grew as well as the wild-type virus. By contrast, the VN1203M2del22, –M2del33, and –M2del44 viruses replicated less efficiently than the wild-type virus (1,000 to 10,000-fold-lower growth). In particular, the VN1203delM2 virus, which lacks both the TM and cytoplasmic tail domains, was significantly growth restricted on MDCK cells (100,000-fold-lower growth than the wild-type virus). These results are consistent with previous findings that mutant viruses with deletions at the C-terminus of the M2 tail grew less well in cell culture (Itwasuki-Horimoto et al., 2006; McCown et al., 2006; McCown et al., 2005).

In vivo growth properties of VN1203 M2 tail deletion mutants. To determine the virulence of the M2 tail mutants, their growth properties in mice were examined. Mice were infected with 100 PFU of M2 mutant or wild-type viruses. On day 3 postinfection, organs were taken from the infected mice for virus titration. As shown in Table 1, the wild-type VN1203 virus replicated well in all organs examined. Mutants possessing deletions of more than 22 amino acids were not recovered from any of the infected mice. Of interest, replication of the VN1203M2del5 and –M2del11 viruses was more than 1 log lower in the lungs, 2 logs lower in nasal turbinates, and 2 logs lower in the kidneys of infected mice than that of wild-type virus. Moreover, no virus was detected from the brain samples of mice infected with the VN1203M2del11 virus. These results indicate that the VN1203M2del 11 virus was attenuated in mice, despite replicating as well as the wild-type virus in MDCK cells.

TABLE 1

Replication of M2 mutant viruses in mice

| Virus | Virus titer (mean log$_{10}$ PFU/g ± SD) in[a]: | | | | |
|---|---|---|---|---|---|
| | Lungs | Nasal turbinates | Brains | Spleens | Kidneys |
| Wild-type | 8.41 ± 0.09 | 6.66 ± 0.85 | 5.02 ± 1.56 | 7.48 ± 0.48 | 6.23 ± 0.82 |
| VN1203M2del5 | 7.47 ± 0.29 | 4.70 ± 1.21 | 3.60, 3.51 | 5.54 ± 0.85 | 3.90, 4.03 |
| VN1203M2del11 | 7.30 ± 0.45 | 4.06, 4.74 | ND[b] | 3.97 ± 0.81 | 4.24 |
| VN1203M2del22 | ND | ND | ND | ND | ND |
| VN1203M2del33 | ND | ND | ND | ND | ND |
| VN1203M2del44 | ND | ND | ND | ND | ND |
| VN1203delM2 | ND | ND | ND | ND | ND |

[a]Mice were infected with 100 PFU of M2 mutant or wild-type virus. Organ samples were taken from mice at day 3 postinfection. Virus titers were determined with M2CK cells. When virus was not recovered from all three mice, individual titers were recorded.
[b]ND, not detected.

Generation of a recombinant VN1203 virus that possesses M2del11 and an avirulent HA. Since the VN1203M2del11 virus was attenuated in mice, the feasibility of using it for an H5N1 vaccine was tested. To improve the safety of an H5N1 virus vaccine, vaccine candidates should have multiple attenuating mutations in the viral genes. Therefore mutations were introduced into the cleavage site of the VN1203M2del11 virus HA, a virulence determinant of influenza viruses in birds and mammals (Hatta et al., 2001; Klenk et al., 1994; Steinhauer et al., 1999). In general, low-pathogenicity viruses do not contain a series of basic amino acids at the HA cleavage site (Klenk et al., 1994; Senne et al., 1996; Steinhauer, 1999), restricting cleavage and viral replication to a limited number of organs (i.e., these viruses cause localized infections). By contrast, the HAs of highly pathogenic H5N1 avian influenza viruses contain a series of basic amino acids at this site (Bosch et al., 1981; Garten et al., 1981; Senne et al., 1996; Suarez et al., 1995), which allow HA to be cleaved not only by trypsin but also by ubiquitous cellular proteases (Horimoto et al., 1994; Stieneke-Grober et al., 1992), thereby allowing viral replication in a variety of organs, including brain (i.e., these viruses cause systemic infections). To ensure the safety of the vaccine strains, a mutant HA was constructed in which the amino acid sequence at the HA cleavage site, PQR-ERRRKKR/G (SEQ ID NO:13), was converted to the sequence in a typical avirulent avian virus, PQ-RETR/G (dashes indicate deletions; SEQ ID NO:14). A recombinant virus possessing this avirulent HA and M2del11 mutations (designated M2del11-HAavir) was generated. Stock virus was amplified on M2CK cells, and the virus titer was 2.0×10$^6$ PFU/mL.

Characterization of the recombinant M2del11-HAavir virus in vitro and in vivo. To characterize the M2del11-HAavir virus, its trypsin dependency in vitro was examined. Plaque assays were performed on M2CK cells in the presence or absence of trypsin. With the M2del11-HAavir virus, clear plaques were visible only in the presence of trypsin, whereas the M2del11 virus formed plaques in both the presence and absence of trypsin (data not shown).

Figure 3:
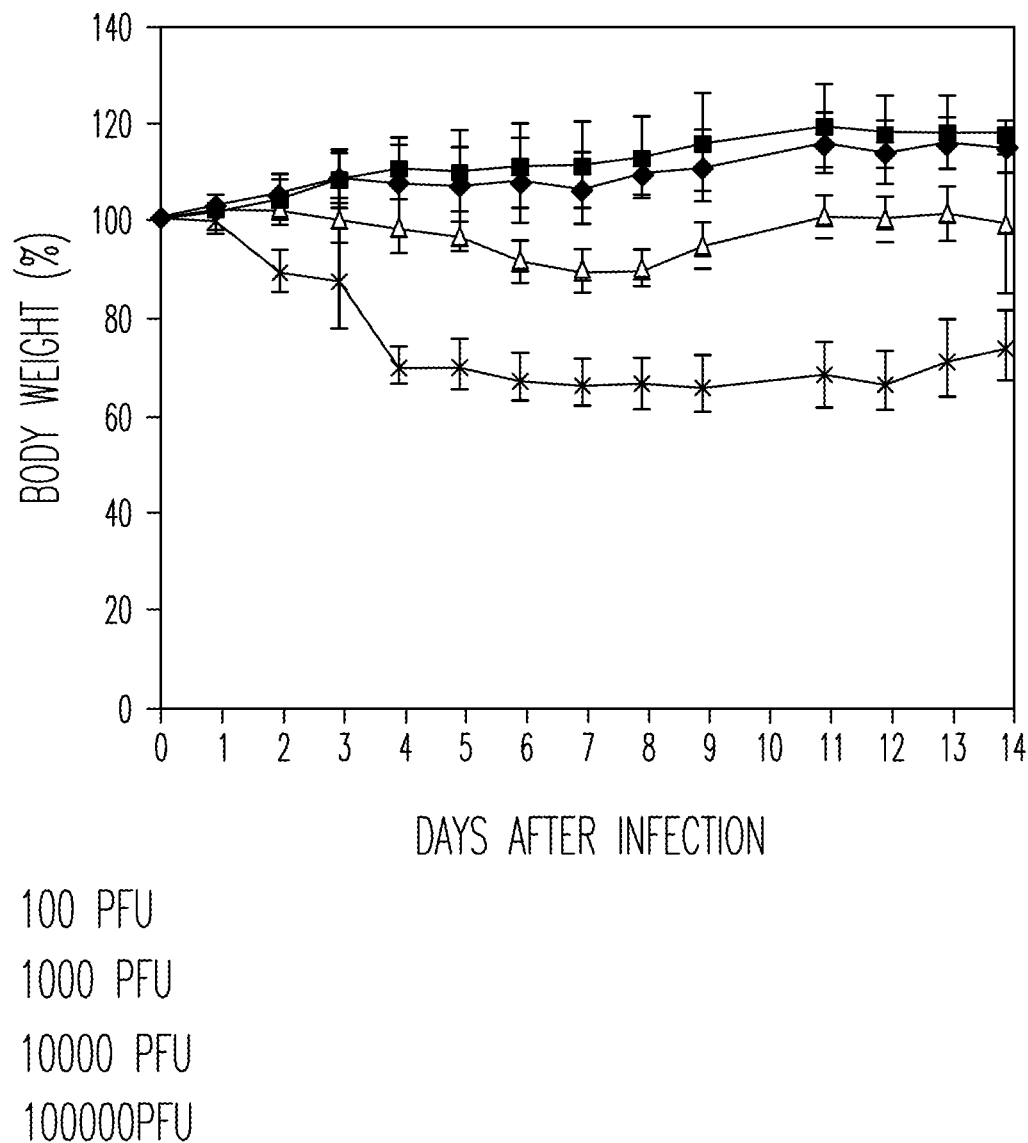
FIG. 3. Pathogenicity of a recombinant M2del11-HAavir virus. Mice were infected with 100, 1,000, 10,000, or 100,000 PFU of the M2del11-HAavir virus, and their body weights were monitored for 14 days. Data are reported as the mean changes in body weight±standard deviation (n=3).

Next, to investigate the virulence of the M2del11-HAavir virus in vivo, mice were infected with various doses of the virus and monitored for 14 days (FIG. 3). Even at a high dose (1×10$^5$ PFU), the virus did not kill any mice (the MLD$_{50}$ was >10$^5$ PFU, compared to 2.1 PFU for the wild-type VN1203 virus [data not shown]), although slight weight loss was observed (FIG. 3). Mice infected with 100 or 1,000 PFU of the M2del11-HAavir virus did not show any weight loss. Organ tropisms for the M2del11-HAavir virus in mice were also examined. As shown in Table 2, the virus titers were 1 log lower in the lungs of mice infected with 100 PFU of the M2del11-HAavir virus than in those of mice infected with the wild-type virus. No virus was detected in the other organs of M2del11-HAavir-infected mice. Even in the mice infected with a high dose (1,000 PFU) of M2del11-HAavir, the virus was recovered only from the lungs and nasal turbinates, indicating that virus replication was restricted to the respiratory tracts. These results suggest that the M2del11-HAavir virus was highly attenuated in mice.

TABLE 2

Replication of M2delII-HAavir virus in mice

| Dose (PFU/mouse) | Virus titer (mean log$_{10}$ PFU/g ± SD) in[a]: | | | | |
|---|---|---|---|---|---|
| | Lungs | Nasal turbinates | Brains | Spleens | Kidneys |
| 100 | 6.38 ± 1.28 | ND[b] | ND | ND | ND |
| 1,000 | 6.77 ± 0.17 | 3.67 ± 1.25 | ND | ND | ND |

[a]Mice were infected with 100 or 1,000 PFU of M2 del11-HAair virus. Organ samples were taken from mice at day 3 postinfection. Virus titers were determined with M2CK cells.
[b]ND, not detected.

Figures 4A, 4B:
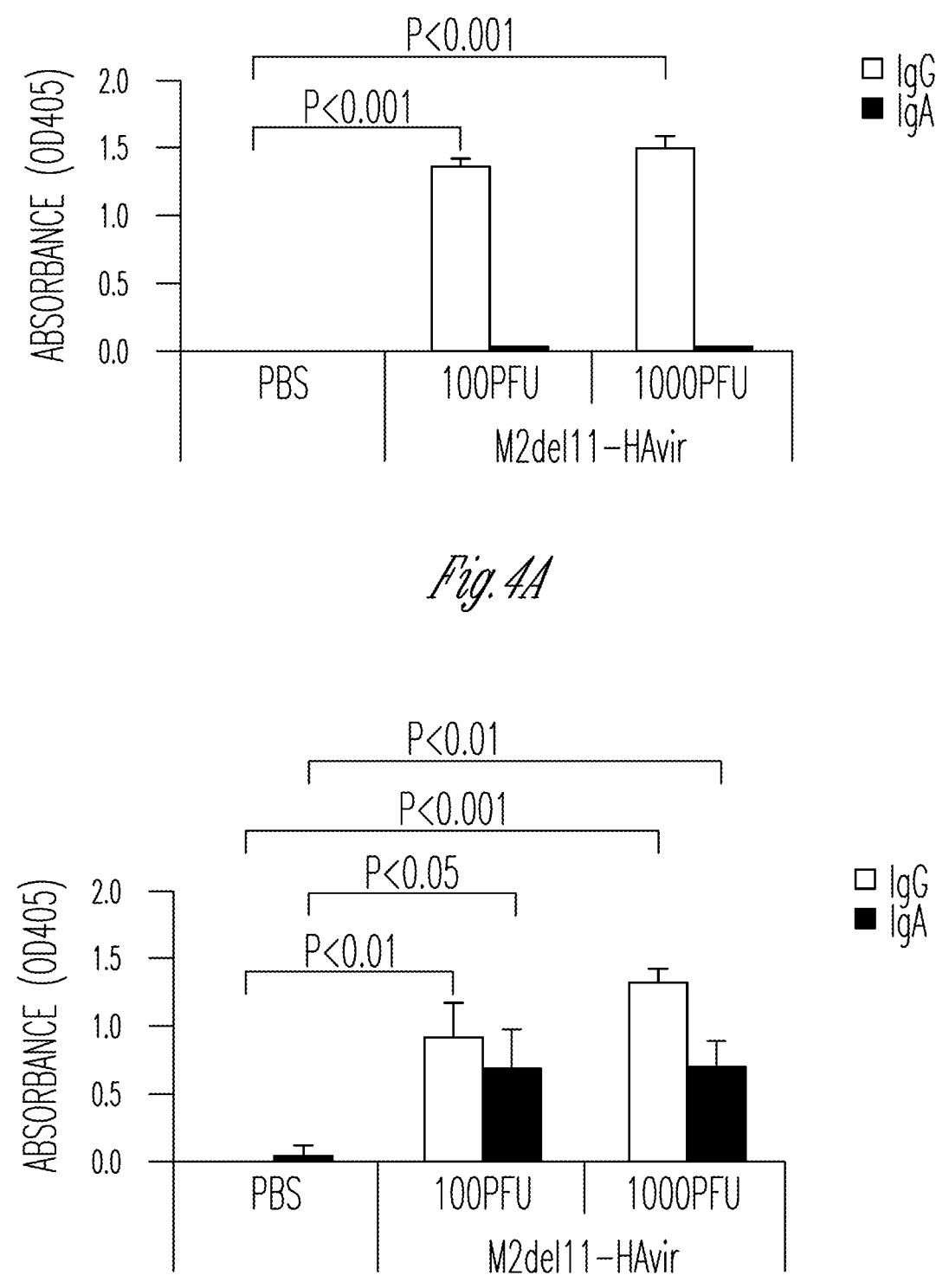
Figure 4C:
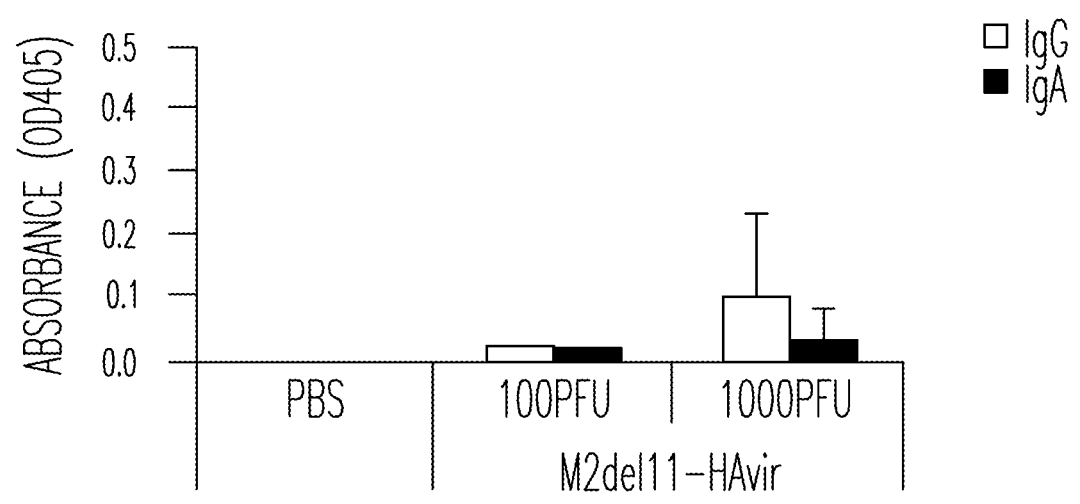

Antibody responses of mice immunized with the M2del11-HAavir virus. To test the efficacy of the M2del11-HAavir virus as a vaccine, mice were intranasally administered with 100 or 1,000 PFU of the M2del11-HAavir virus. Three weeks later, IgG and IgA levels in sera, trachea-lung washes, and nasal washes of immunized mice were measured by means of an ELISA (FIG. 4). Both IgG and IgA levels in trachea-lung washes were significantly higher in mice immunized with the M2del11-HAavir virus than in those treated with a PBS control, although there was no significant difference between the antibody titers in nasal washes from the vaccine group and the control group. The IgA response was negligible in serum, regardless of the dose of the mutant virus used for immunization, but IgG production was clearly higher in mice inoculated with the M2del11-HAavir virus. These data suggest that the M2del11-HAavir virus elicited a significant antibody response in the immunized mice.

To examine whether or not the antibodies detected by ELISA contribute to neutralization of the H5N1 virus infectivity, the infectivity-neutralizing activity of the samples against VN1203 (homologous virus; clade 1) and A/Indonesia/ July 2005 (Indonesia 7) (heterologous virus; clade 2), whose HA homology is 96.5% at the amino acid level was tested Immunization with 1,000 PFU of M2del11-HAavir virus did not elicit neutralizing antibody efficiently, and the reciprocal titers of serum required to neutralize 50% of VN1203 and Indonesia 7 were only 31 and 23, respectively (data not shown). Moreover, no neutralizing antibody was detectable in sera from mice immunized with 100 PFU of M2del11-HAavir virus (data not shown), indicating that only a limited level of neutralizing antibody was elicited upon immunization of mice with the M2del11-HAavir virus despite high levels of protection upon lethal challenge and high levels of IgG detected by ELISA.

Protective efficacy of the M2del1-HAavir virus in mice. Mice immunized with the M2del11-HAavir virus were challenged 1 month after immunization with 100 $MLD_{50}$ of the wild-type VN1203 virus (clade 1) or Indonesia 7 (clade 2). Unlike control mice, all M2del11-HAavir-immunized mice survived a lethal challenge with either of the highly pathogenic H5N1 viruses (data not shown) and did not show any symptoms, including weight loss, after the challenge. By contrast, all of the control mice died or had to be euthanized due to their symptoms by day 8 postchallenge (data not shown). The virus titers in several organs of the mice challenged with the VN1203 or Indonesia 7 vines (Table 3) was also determined. High titers of viruses were recovered from all organs of the control group. No virus was detected from any of the organs in the M2del11-HA virus vaccine group challenged with VN1203, though a limited amount of virus was detected in the nasal turbinates of one of the immunized mice challenged with the Indonesia 7 virus (Table 2). Taking the results together, it was concluded that the M2del11-HAavir virus can confer protective immunity to mice against lethal challenge with highly pathogenic H5N1 virus.

Those findings indicate that the M2 cytoplasmic tail has a vital role(s) in virus replication in animals and that M2 tail mutants could be good vaccine candidates for influenza virus infection. Here, it was demonstrated that H5N1 M2del11-HAavir virus, which has an 11-amino-acid deletion from the C-terminus of its M2 protein and an avirulent HA. protected mice from a lethal challenge with H5N1 viruses, indicating its considerable potential as a live virus vaccine against highly pathogenic H5N1 viruses.

Recently, Suguitan et al. (2006) tested the vaccine efficacy in mice and ferrets of live attenuated, cold-adapted virus vaccine candidates that possess the modified avirulent type of HA and the NA from H5N1 strains, together with the internal genes from cold-adapted A/Ann Arbor/6/60 (H2N2). They demonstrated that a single dose of the vaccine protected animals from lethality but did not fully protected them from replication of the challenge H5N1 viruses, indicating limited efficacy for single-dose vaccination of these cold-adapted viruses. This incomplete protection may stem from unmatched antigenicity between the internal proteins of the cold-adapted virus (i.e., derived from H2N2 virus) and the challenge virus. Here, it was shown that the M2del11-HAavir virus, whose eight genes are derived from an H5N1 virus, protects mice almost completely from replication of heterologous H5N1 virus as well as homologous virus (Table 7). Despite its complete protection, the M2del11-HAavir virus did not elicit neutralizing antibody against either homologous or heterologous viruses efficiently, whereas it elicited high levels of antibodies detected by ELISA. Therefore, cytotoxic T-lymphocyte responses specific to viral internal proteins that contain common cytotoxic T-lymphocyte epitopes among influenza A viruses (i.e., NP and M proteins) and mucosal immune responses may be responsible for the cross-protection observed in this study, as suggested in Takeda et al. (2003). If a vaccine against pandemic influenza is introduced only once a pandemic is imminent, all of the eight genes of the vaccine candidates could be derived from the pandemic strain to offer optimal protection to humans from virus infection. To reduce the risk of the emergence of the revertants, live attenuated virus vaccines should have multiple attenuating mutations in the genes that encode their internal proteins. NS1 mutant viruses are highly attenuated in mice because they lack interferon antagonist activity while retaining the ability to induce protective immunity against influenza virus challenge (Talon et al., 2000). Hence, by combining a mutant NS1 protein with the M2 tail deletion mutants identified in this study, an improved "master" influenza virus could be produced as a first step in the production of safe live influenza

TABLE 3

Replication of M2 mutant viruses in mice

| Challenge Virus | Group | Virus titer (mean $log_{50}$ PFU/g ± SD) in[a]: | | | | |
|---|---|---|---|---|---|---|
| | | Lungs | Nasal turbinates | Brains | Spleens | Kidneys |
| VN1203 | PBS | 7.83 ± 0.46 | 6.11, 4.19 | 3.04 | 4.96 ± 0.66 | 2.78, 4.27 |
| | M2del11-HAavir | | | | | |
| | 100 PFU | ND[b] | ND | ND[b] | ND | ND |
| | 1,000 PFU | ND | ND | ND | ND | ND |
| Indonesia 7 | PBS | | | | | |
| | M2del11-HAavir | 9.06 ± 0.10 | 7.01 ± 0.21 | 3.32 ± 1.37 | 5.64 ± 0.12 | 4.27 ± 0.38 |
| | 100 PFU | ND | ND | ND | ND | ND |
| | 1,000 PFU | ND | 1.96 | ND | ND | ND |

[a]Three mice from each group were sacrificed on day 3 postchallenge for virus titration. When virus was not recovered from all three mice, individual titers were recorded.
[b]ND, not detected.

Discussion

The influenza A virus M2 is a multifunctional protein. It has ion channel activity in its TM domain (Pinto et al., 1982), which is thought to function at an early stage of replication (acidification of the virion interior) (Helenius, 1992; Martin et al., 1991; Sugrue et al., 1991) and at a late stage (protection of an acid-mediated conformational change of cleaved HA) (Hay et al., 1985; Ohuchi et al., 1994; Takeuchi et al., 1991). In addition, its cytoplasmic tail is important for viral assembly (Itwasuki-Horimoto et al., 2006; McCown et al., 2006; McCown et al., 2005). In this study, a series of M2 tail deletion mutants was generated and their growth properties in vitro and in vivo examined. Deletions of 5 or 11 amino acids from the C-terminus of M2 were found to not affect virus replication in cell culture but inhibited virus growth in mice. Previously it was shown that even one amino acid deletion from the M2 C-terminus attenuated influenza virus in ferrets (Castrucci et al., 1995).

vaccines. Continued progress in understanding the functions of these influenza virus proteins should allow the introduction of multiple mutations in live vaccine strains, in addition to those in the HA, NS, and M genes, thereby reducing the likelihood of the emergence of pathogenic revertant viruses.

For live attenuated H5N1 virus vaccines to be clinically useful, the binding specificity of H5 HA for α-2,3-linked sialic acid (SA) receptors, which are preferentially recognized by avian influenza virus and rarely present in the upper respiratory tract of humans (Conner et al., 1994; Rogers et al., 1989; Rogers et al., 1983), must be considered. To address this problem, one could modify the H5 HA to alter its specificity for SA receptors. Recently, Auewarakul et al. (2007); Yamada et al. (2006); Yang et al. (2007) have determined specific amino acids in the avian H5 HA that alter its receptor-binding specificity toward α-2,6-SA (human-type receptor) recognition. This strategy may allow the generation of a recombinant H5N1-based vaccine that recognizes human-type α-2,6-SA receptors and efficiently replicates in the upper respiratory tract in humans.

EXAMPLE 2

Several lines of evidence suggest that the M2 protein of influenza A virus is responsible for key steps in the viral life cycle (Hay et al., 1985; Iwatsuki-Horimoto et al., 2006; Martin et al., 1991; McCown et al., 2005; Ohuchi et al., 1994; Sugrue et al., 1991; Takeuchi et al., 1994). Indeed, it has previously been shown that the influenza A virus that lacks the TM and cytoplasmic tail domains (M2 knockout [M2KO]) of M2 is highly attenuated in cell culture and in mice compared to the wild-type virus (Iwatsuki-Horimoto et al., 2000; Watanabe et al., 2001). The potential of M2KO influenza A virus as a live attenuated vaccine was examined by immunizing mice and testing immune responses and protective efficacy in a mouse model experimentally infected with A/Puerto Rico/8/34 (PR8), a highly lethal virus in mice.

Figure 7A:
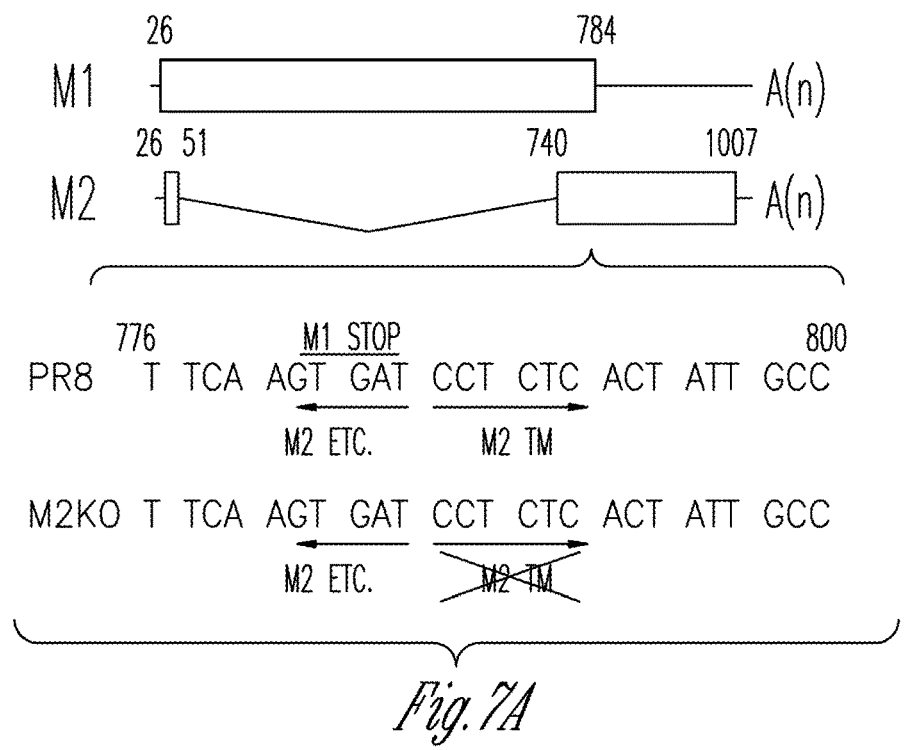
FIGS. 7A-7C. Construction of the mutant M segment, growth kinetics of M2KO virus, and change in body weight of mice infected with M2KO virus. (A) Schematic diagram of the mutated M segment of the M2KO virus. Blue and yellow columns represent the open reading frame of the M1 and M2 proteins, respectively. Two stop codons (TGA TGA) were introduced downstream of the open reading frame of the M1 protein in the M segment to eliminate the TM and cytoplasmic tail domains of the M2 protein. M2 ect., M2 TM, and A (n) denote the ectodomain domain of M2, the TM domain of M2, and the poly(A) tail, respectively. Numbers refer to the nucleotide numbers from the 5' end of the cRNA. (B) Growth properties of PR8 and M2KO vinises in MDCK and M2-expressing MDCK (M2CK) cells. MDCK and M2CK cells were infected with PR8 or M2KO virus at a multiplicity of infection of 0.001. Virus titers in the supernatant of MDCK (left) and M2CK (right) cells at various time points postinfection were determined by using M2CK cells. The dotted line indicates the detection limit of virus titer (10 PFU/ml). (C) Body weight changes in mice inoculated with PBS, PR8, or M2KO virus. The body weights of the control (PBS) or infected (PR8 or M2KO virus) mice were measured daily postinfection. Values are expressed as the mean change in body weight±standard deviations (n=8 for PBS and M2KO virus; n=3 for PR8).
Figure 7B:
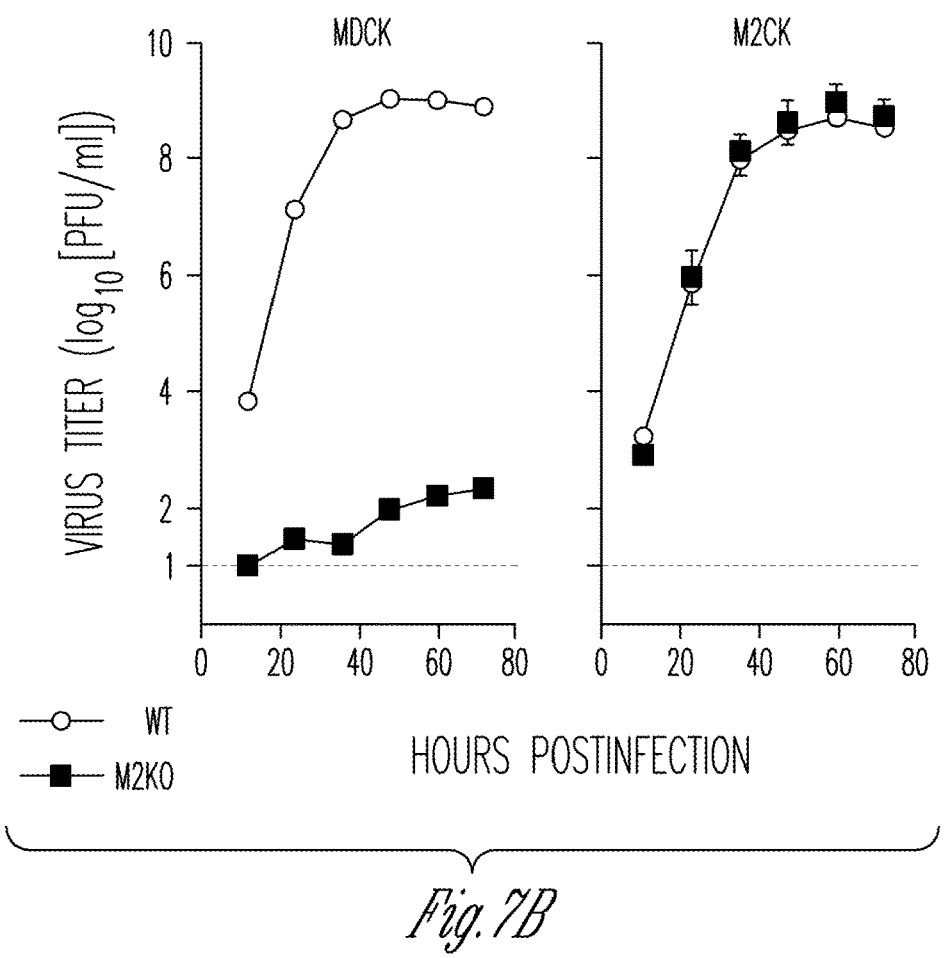

To generate the M2KO virus, two stop codons were inserted in the M gene segment downstream of the open reading frame of the M1 protein to remove the TM and cytoplasmic tail domains of the M2 protein (FIG. 7A). Then, wild-type PR8 and M2KO viruses were generated by plasmid-based reverse genetics (Neumann et al., 1999). To confirm attenuation of the M2KO virus, the PR8 and M2KO viruses were inoculated into both MDCK and M2CK cells (Iwatsuki-Horimoto et al., 2001) at a multiplicity of infection of 0.001, and virus titers were determined at various times postinfection by using M2CK cells (FIG. 7B). M2KO virus was highly attenuated in MDCK cells (FIG. 7B, left) but replicated as well as the wild-type virus in M2CK cells (FIG. 7B, right). These data suggest that the M2KO virus is highly attenuated in normal cells but that high titer virus stocks can be produced in cells expressing the M2 protein.

Figure 7C:
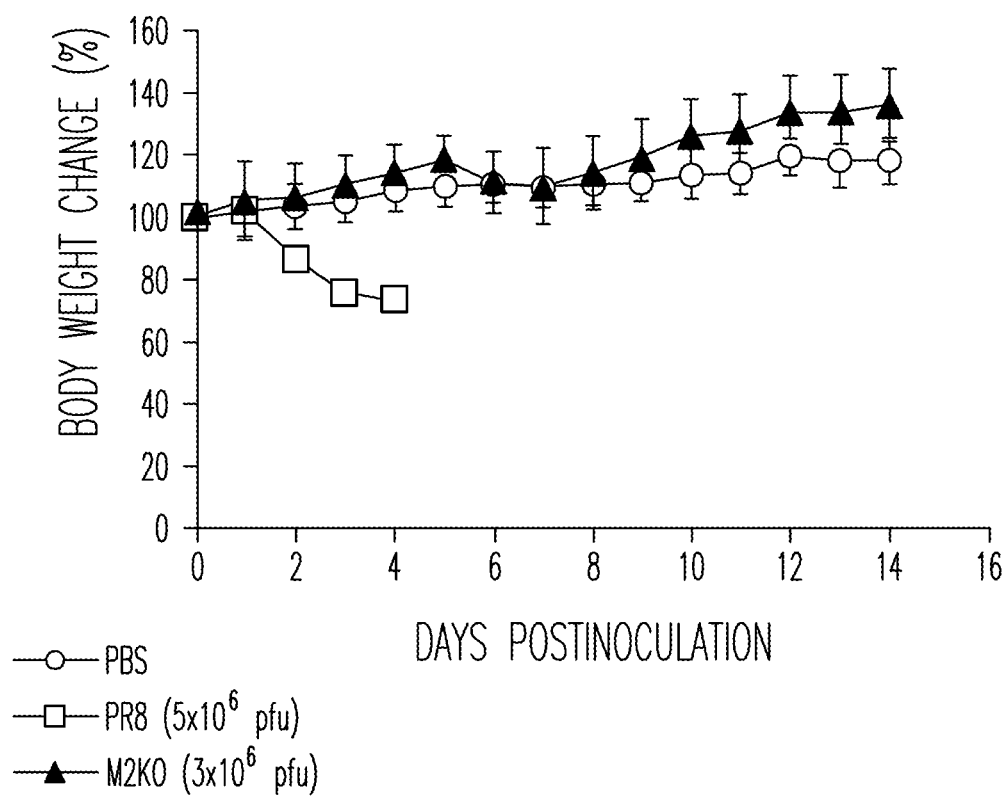

Attenuation of viruses in animals is essential for live vaccines. The pathogenicity of the M2KO virus was examined in mice. 4-week-old female BALB/c mice were intranasally infected with different doses of M2KO virus and the virus titers in lungs and nasal turbinates determined. Body weights were also monitored. When mice were infected with even $3\times10^6$ or $3\times10^5$ PFU of virus, virus was recovered from the lungs, but titers were significantly lower than those in the lungs of mice infected with PR8 (P<0.05) (Table 4). By day 8 postinfection, M2KO virus was no longer detected in the lungs (data not shown). Although virus was recovered from the lungs of one of the animals infected with $3\times10^4$ PFU of virus, virus was not detected from any mice infected with lower titers (i.e., $3\times10^2$ or $3\times10^3$ PFU) of M2KO virus (Table 4 and data not shown). In nasal turbinates, no virus was recovered from any mice inoculated with the M2KO virus on days 3 and 6 postinfection (Table 4). The body weights of mice infected with $5\times10^6$ PFU of PR8 rapidly decreased, and these mice were euthanized by 4 days postinfection (FIG. 7C). On the other hand, mice infected with $3\times10^6$ PFU of M2KO virus showed no body weight loss (FIG. 7C). Taken together, these data indicate that the M2KO virus is highly attenuated in mice, satisfying its requirement for a live attenuated influenza vaccine.

TABLE 4

Replication of M2KO virus in mice[a]

| Virus | PFU of virus inoculated per mouse | Days postinfection | Virus titer (mean ± SD log$_{10}$ [PFU/g]) from indicated source[b] | |
|---|---|---|---|---|
| | | | Lungs | Nasal turbinates |
| PR8 | $1 \times 10^3$ | 3 | 8.5 ± 0.1 | 6.0, 5.8 |
| | $1 \times 10^3$ | 6 | 7.0 ± 0.1 | 6.4 ± 0.2` |
| M2KO | $3 \times 10^6$ | 3 | 5.7 ± 0.3 | ND |
| | $3 \times 10^6$ | 6 | 5.5 ± 0.3 | ND |
| | $3 \times 10^5$ | 3 | 4.1 ± 0.2 | ND |
| | $3 \times 10^5$ | 6 | 5.3, 4.2 | ND |
| | $3 \times 10^4$ | 3 | 5.2 | ND |
| | $3 \times 10^4$ | 6 | ND | ND |

[a]Three BALB/c mice per group were intranasally infected with the indicated amounts of virus (50 µL per mouse) and sacrificed on days 3 and 6 prostinfection for virus titration. When virus was not recovered from all three mice, individual titers were recorded. On day 3 postinfection, virus was not recovered from organs of mice infected with either $3 \times 10^2$ or $3 \times 10^3$ PFU of M2KO virus (data not shown).
[b]ND, not detected (detection limit, 10 PFU/mL/lung).

Figure 8A:
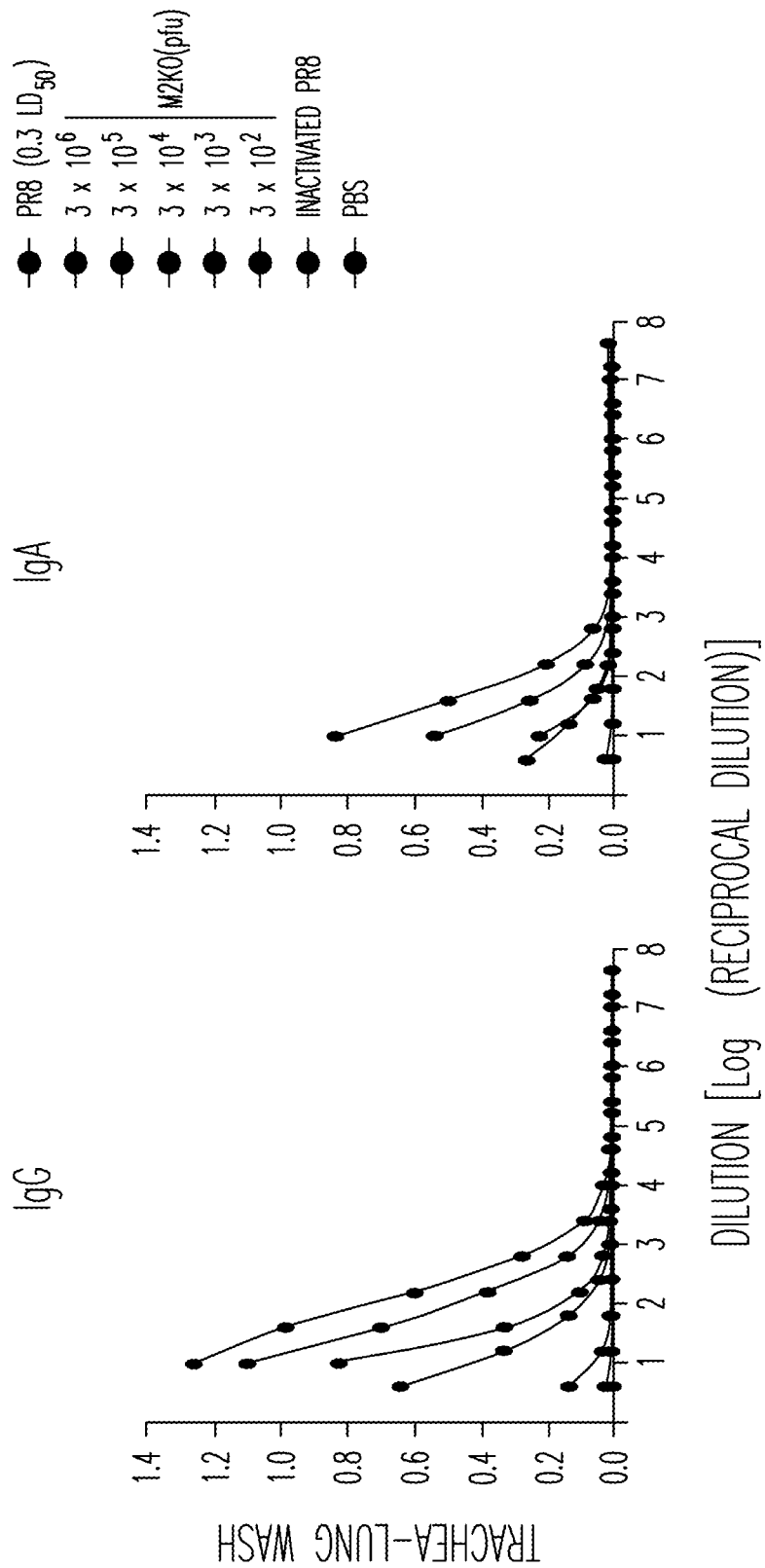
FIGS. 8A-8C. Virus-specific antibodies in trachea/lung and nasal washes and in sera of mice inoculated with M2KO virus. Samples from each group were obtained 4 weeks postimmunization. Samples were serially diluted, and IgG and IgA in samples from individual mice were detected by use of an enzyme-linked immunosorbent assay. Values are expressed as mean absorbances (n=4).
Figure 8B:
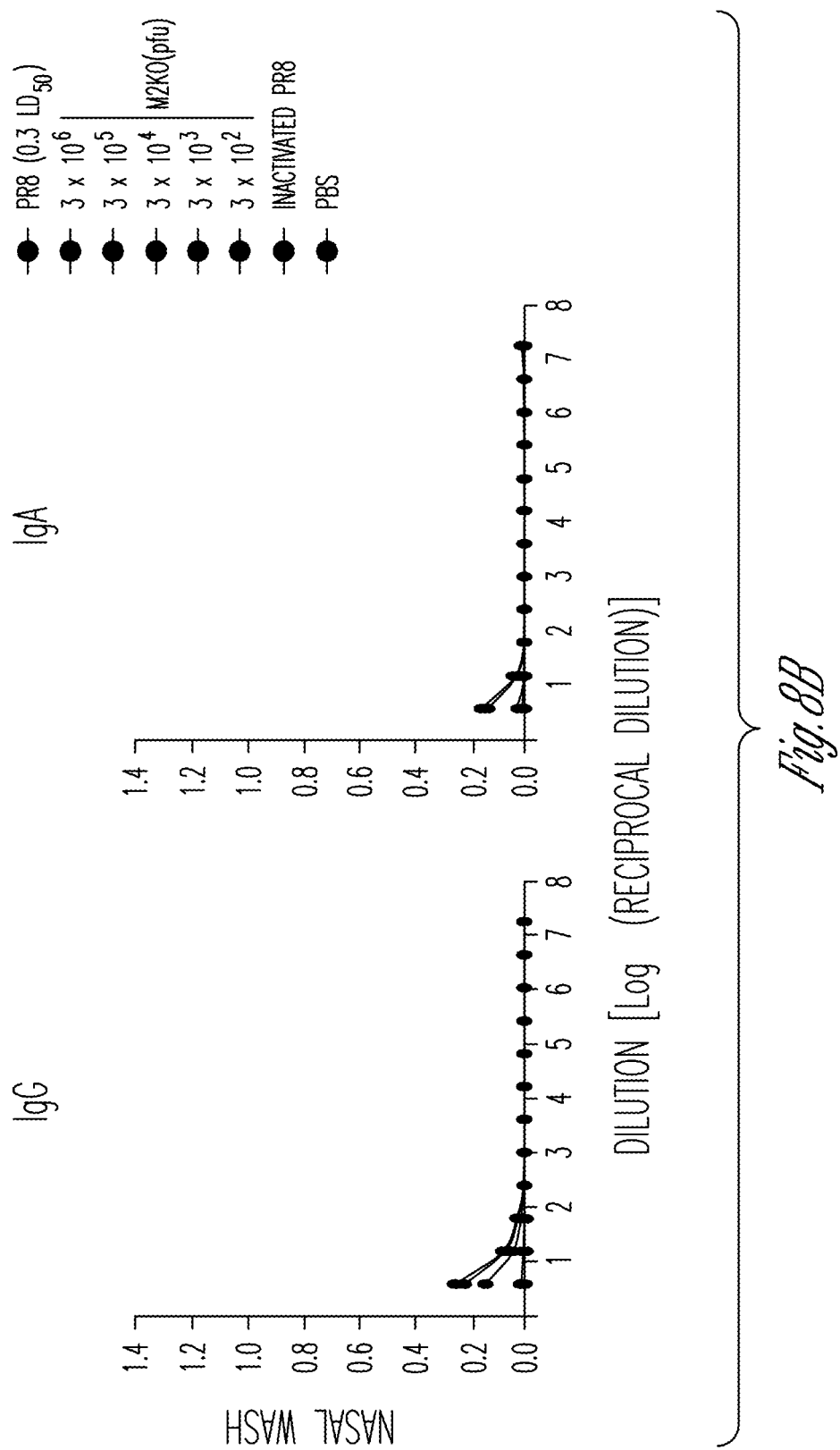
Figure 8C:
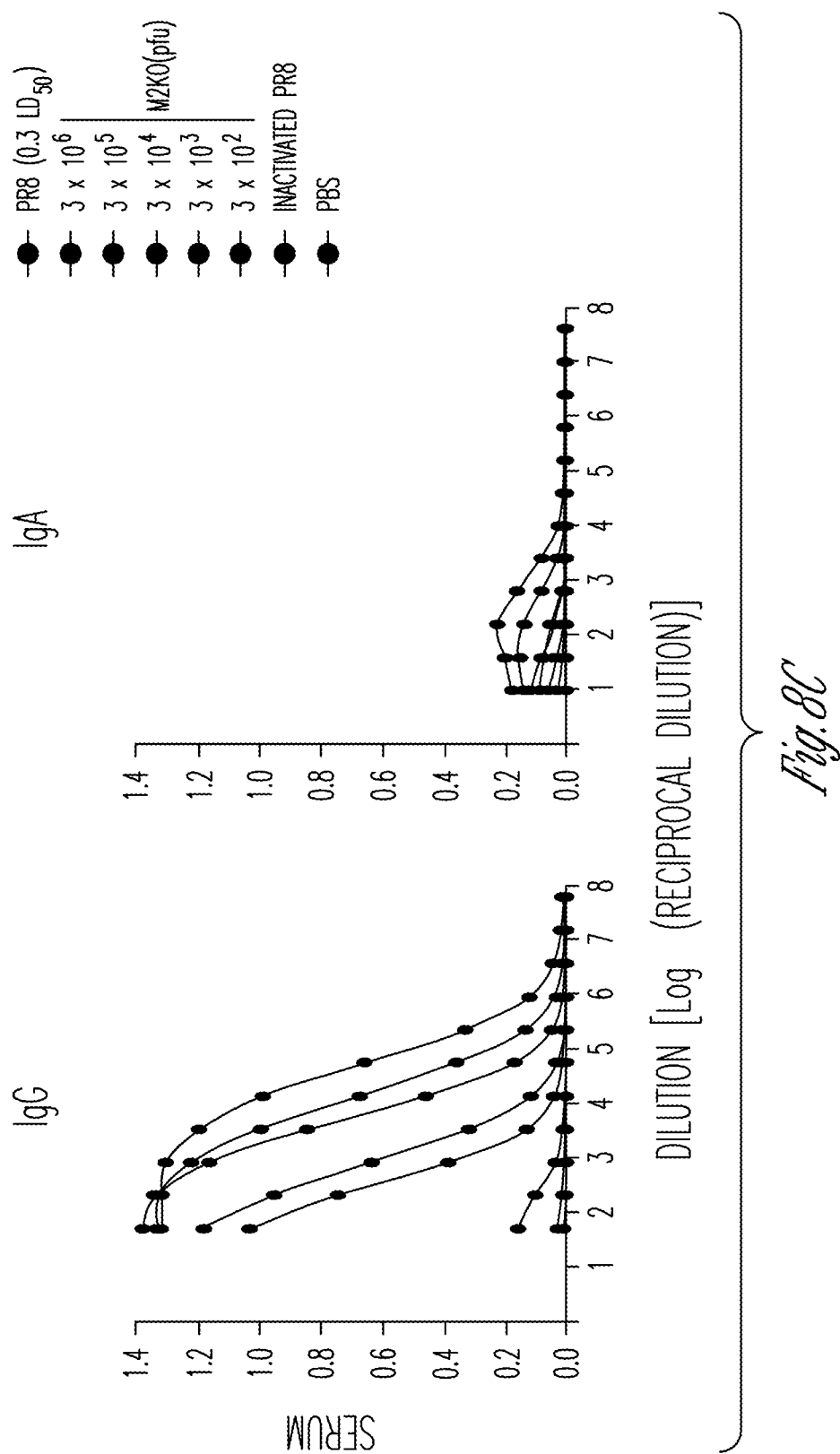

The level of antibody responses elicited by the M2KO virus was also determined. 4-week-old female BALB/c mice were intranasally inoculated with different doses of M2KO virus. As negative and positive controls, mice were also intranasally inoculated with phosphate-buffered saline (PBS) or a dose equivalent to $3\times10^6$ PFU of formalin-inactivated PR8 (32 hemagglutination units), and a 50% mouse lethal dose of PR8 of 0.3 (500 PFU), respectively. Four weeks after inoculation, titers of immunoglobulin G (IgG) and IgA antibodies against PR8 in sera, trachea/lungs, and nasal washes were determined by an enzyme-linked immunosorbent assay (FIG. 8). Neither the IgG nor the IgA response was appreciable in negative control mice (PBS and inactivated PR8). Although IgG and IgA titers in mice infected with a 50% mouse lethal dose of PR8 of 0.3 were higher, those in mice inoculated with $3\times10^6$ PFU of M2KO virus were also similarly increased. Moreover, antibody responses correlated with the doses of M2KO virus, although responses in mice inoculated with $3\times10^2$ PFU of M2KO virus were limited.

To assess the protective efficacy of M2KO virus, mice intranasally inoculated with M2KO virus, formalin-inactivated PR8, or PBS were challenged with a lethal dose of PR8 at 4 and 12 weeks postimmimization. Virus titers in lungs and nasal turbinates of challenged mice were determined by using MDCK cells 3 days postchallenge. Virus could not be detected in organs of mice inoculated either with $3\times10^6$ or $3\times10^5$ PFU of M2KO viruses, indicating that vaccination with these amounts of M2KO virus gave mice sterile immunity (Table 5). All mice immunized with lower doses ($3\times10^4$ and $3\times10^3$ PFU), with the exception of one mouse inoculated with $3\times10^3$ PFU of virus, survived a lethal challenge, although virus was detected in both organs tested and the amounts of virus were not significantly lower than those in the control mice (Table 2). This is probably because virus clearance later than day 3 postchallenge (the time point at which organ virus titers were examined) was more efficient in these immunized mice than that in the control mice. Indeed, although these mice lost body weight until 7 days postchallenge, they ultimately regained their body weight (data not shown). Taken together, the data indicate that M2KO virus confers effective protection against challenge with a lethal dose of PR8.

TABLE 5

Protection against challenge with lethal doses of PR8 in mice immunized with M2KO virus[a]

| Weeks post-immunization | Immunogen | PFU of virus inoculated per mouse | No. of survivors/no. of mice tested | Virus titer (mean ± SD $\log_{10}$ ([PFU/g]) from indicated source[c] | |
|---|---|---|---|---|---|
| | | | | Lungs | Nasal turbinates |
| 4 | M2KO | $3 \times 10^6$ | 8/8 | ND | ND |
| | M2KO | $3 \times 10^5$ | 8/8 | ND | ND |
| | M2KO | $3 \times 10^4$ | 8/8 | 6/3 ± 1.5 | 5.1 ± 0.3 |
| | M2KO | $3 \times 10^3$ | 7/8 | 6.9, 6.6 | 6.2, 6.0 |
| | M2KO | $3 \times 10^2$ | 0/8 | 8.0 ± 0.1 | 6.3 ± 0.3 |
| | Inactivated PR8[b] | | 0/8 | 7.6 ± 0.1 | 5.9 ± 0.2 |
| | PBS | | 0/8 | 7.5 ± 0.1 | 5.9 ± 0.1 |
| 12 | M2KO | $3 \times 10^6$ | 8/8 | ND | ND |
| | M2KO | $3 \times 10^5$ | 8/8 | ND | ND |
| | M2KO | $3 \times 10^4$ | 8/8 | 7.2 ± 0.6 | 6.0 ± 0.3 |
| | M2KO | $3 \times 10^3$ | 7/8 | 7.4 ± 0.6 | 6.3 ± 0.2 |
| | M2KO | $3 \times 10^2$ | 0/8 | 8.5 ± 0.2 | 6.9 ± 0.2 |
| | Inactivated PR8 | | 0/8 | 7.3 ± 0.2 | 6.7 ± 0.3 |
| | PBS | | 0/8 | 7.8 ± 0.3 | 6.2 ± 0.6 |

[a]Twenty-two BALB/c mice per group were intranasally immunized with the indicated amounts of M2KO virus, inactivated PR8, or PBS (50 μl per mouse). Half of the mice were challenged with a 50% lethal dose of wild-type PR8 of 100, 4 weeks postimmunization, and the remaining mice were challenged 12 weeks postimmunization. Eight mice per group were monitored for survival for 14 days after challenge. Three mice per each group were sacrificed on day 3 postchallenge to measure virus titration. When virus was not recovered from all three mice, individual titers were recorded.
[b]Virus particles equivalent to $3 \times 10^6$ PFU (32 hemagglutination units) were used.
[c]ND, not detected (detection limit, 10 PFU/mL/lung).

Thus, M2KO influenza virus that lacks the TM and cytoplasmic tail domains of the M2 protein can be used as a live attenuated influenza vaccine. It appears to be considerably safe and strongly immunogenic. Moreover, the growth profile of this virus is indistinguishable from that of the parent virus (PR8) in cells stably expressing the wild-type M2 protein, suggesting the feasibility of efficient vaccine production, although the cell line expressing the M2 protein may need to be validated for the lack of unwanted properties, such as the presence of adventitious agents and tumorigenicity, prior to its use in vaccine production for humans.

Embryonated hen eggs are currently used for the manufacture of the vaccine; however, they have potentially serious problems. One of the major problems is that cultivation of viruses in eggs can lead to the selection of variants that are antigenically distinct from viruses grown in mammalian cells (Katz et al., 1987; Robinson et al., 1985; Schild et al., 1983). In addition, there is a risk of allergic sensitization and reactions to egg proteins present in vaccines made from embryonated eggs. However, isolation of human influenza viruses from mammalian cells allows one to obtain viruses that are closely related to those present in clinical specimens of influenza patients (Katz et al, 1990; Robertson et al., 1990; Robertson et al., 1991). In addition, it has been demonstrated that inactivated vaccines prepared from cell-grown viruses induce greater cross-reactive serum antibody and cellular responses or protect better than those made from egg-grown viruses compared in animal models (Alymora et al., 1998; Bruhl et al, 2000; Katz et al., 1989; Wood et al., 1989). The fact that M2KO virus amplification relies on cells stably expressing the wild-type M2 protein demonstrates its suitability for vaccine production and solves many of the problems associated with vaccines made from embryonated eggs.

There has always been a question regarding the safety of live influenza vaccines due to possible reassortment between field strains and attenuated vaccine strains during epidemics and pandemics. However, such concerns are unfounded because even if reassortment occurs, as long as the backbone virus for the live vaccines is less pathogenic than the field strains, the pathogenicity of the resultant reassortant would be the same or less than that of the field strain.

Recent outbreaks of highly pathogenic H5N1 avian influenza virus pose a serious threat to human health. Although several clinical trials using inactivated H5 vaccine have been conducted (Bressen et al., 2006; Lin et al., 2006; Nicholson et al., 2001; Stephanson et al., 2003; Treanor et al., 2006), the efficacy of inactivated vaccines against such highly pathogenic viruses in immunologically naïve populations remains unknown. It is important to explore live vaccines, which could provide better protective immunity than inactivated vaccines due to their ability to provide mucosal and cellular immune responses. The M2KO vaccine disclosed here, together with the M2 cytoplasmic tail mutant vaccine that was recently reported (Watanabe et al., 2008), may set the stage for further development of live attenuated H5 influenza vaccines.

REFERENCES

Alymova et al., *J. Virol.*, 72:4472 (1998).
Auewarakul et al., *J. Virol.*, 81:9950 (2007).
Bilsel et al., *J. Virol.*, 67:6762 (1993).
Bosch et al., *Virology*, 113:725 (1981).
Bresson et al., *Lancet*, 367:1657, (2006).
Brühl et al., *Vaccine*, 19:1149 (2000).
Castrucci et al., *J. Virol.*, 69:2725 (1995).
Centers for Disease Control and Prevention. 2007. Expansion of use of live attenuated influenza vaccine (FluMist) to children aged 2-4 years and other FluMist changes for the 2007-08 influenza season. Morb. Mortal. Wkly. Rep. 56:1217-1219.
Connor et al., *Virology*, 205:17 (1994).
Cox et al., Influenza. *Lancet*, 354:1277 (1999).
Cox et al., *Scand. J. Immunol.*, 59:1 (2004).
Cox et al., *Virology*, 167:554 (1988).
Garten et al., *Virology*, 115:361 (1981).
Hatta et al., *Science*, 293:1840 (2001).
Hay et al., (eds) *Options for the control of influenza II.* Excerpta Medica, Amsterdam, pp. 281-288 (1993).
Hay et al., *EMBO J.*, 4:3021 (1985).
Helenius, *Cell*, 69:577 (1992).
Holsinger et al., *J. Virol.* 68:1551 (1994).
Horimoto et al., *J. Virol.*, 68:3120 (1994).
Iwatsuki-Horimoto et al., *J. Virol.*, 80:5233 (2006).
Katz et al., *J. Infect. Dis.*, 160:191 (1989)
Katz et al., *J. Virol.* 64:1808 (1990).
Katz et al., *Virology*, 156:386 (1987).
Kida et al., *Virology.* 122:38 (1982).
Klenk et al., *Trends Microbiol.*, 2:39 (1994).
Lamb et al., *Cell*, 40:627 (1985).
Lin et al., *Lancet*, 368:991 (2006).
Martin et al., *Cell.* 67:117 (1991).

McCown et al., *J. Virol.*, 79:3595 (2005).
McCown et al., *J. Virol.*, 80:8178 (2006).
Neumann et al., *Proc. Natl. Acad. Sci. USA*, 96:9345 (1999).
Nicholson et al., *Lancet*, 357:1937 (2001).
Ohuchi et al., *J. Virol.*, 68:920 (1994).
Pinto et al., *Cell*, 69:517 (1992).
Robertson et al., *J. Gen. Virol.*, 72:2671 (1991).
Robertson et al., *Virology*, 143:166 (1985).
Robertson et al., *Virology*, 179:35 (1990).
Rogers et al., *Virology*, 127:361 (1983).
Rogers et al., *Virology*, 173:317 (1989).
Schild et al., *Nature*, 303:706 (1983).
Schnell et al., *EMBO J.*, 13:4195 (1994).
Seine et al., *Avian Dis.*, 40:425 (1996).
Steinhauer, *Virology*, 258:1 (1999).
Stephenson et al., *Vaccine*, 21:1687 (1983).
Stieneke-Grober et al., *EMBO J.*, 11:2407 (1992).
Strebel et al., *J. Virol.*, 63:3784 (1989).
Suarez et al., *J. Virol.*, 72:6678 (1998).
Sugrue et al., *EMBO J.*, 9:3469 (1990).
Sugrue et al., *Virology*, 180:617 (1991).
Suguitan et al., *PLoS Med.* 3:e360 (2006).
Takada et al., *Vaccine*, 21:3212 (2003).
Takeuchi et al., *J. Virol.*, 68:911 (1994).
Talon et al., *Proc. Natl. Acad. Sci. USA*, 97:4309 (2000).
Treanor et al., *N. Engl. J. Med.* 354:1343 (2006).
Watanabe et al., *J. Virol.*, 75:5656 (2001).
Watanabe et al., *J. Virol.*, 82:2486 (2008).
Wood et al., *Virology.* 171:214 (1989).
World Health Organization. 2006. Avian influenza A (H5N1). *Wkly. Epidemiol. Rec.*, 81:249-260.
Yamada et al., *Nature*, 444:378 (2006).
Yang et al., *Science.* 317:825 (2007).
Zebedee et al., *J. Viral.*, 56:502 (1985).
Zebedee et al., *J. Virol.*, 62:2762 (1988).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A vaccine comprising an effective amount of a live, attenuated isolated recombinant influenza virus comprising a mutant M gene segment that is mutated so that upon viral replication the mutant M gene expresses a functional M1 protein and a mutant M2 protein comprising an extracellular domain or a portion thereof, a deletion of a cytoplasmic tail and either lacking a transmembrane domain or having a mutated transmembrane domain,
wherein (a) the mutant M2 protein further comprises a heterologous protein at the C-terminus of the extracellular domain, (b) the mutant M2 protein further comprises a heterologous immunogenic protein of a pathogen, (c) the recombinant influenza virus comprises a hemagglutinin (HA) that is modified at the HA cleavage site, (d) the recombinant influenza virus further comprises another attenuating mutation, (e) the recombinant influenza virus comprises a HA that is a heterologous HA, or (f) the recombinant influenza virus comprises a neuraminidase (NA) that is a heterologous NA.

2. The vaccine of claim 1 wherein the mutant M2 protein consists of the M2 extracellular domain.

3. The vaccine of claim 1 wherein the M2 extracellular domain or the portion thereof comprises less than 24 residues.

4. The vaccine of claim 1 wherein the portion of the M2 extracellular domain comprises at least 9 residues.

5. The vaccine of claim 1 wherein the mutation in the transmembrane domain comprises at least one amino acid substitution.

6. The vaccine of claim 1 wherein the mutation in the transmembrane domain comprises a deletion in the transmembrane domain.

7. The vaccine of claim 1 wherein the recombinant influenza virus comprises influenza A HA.

8. The vaccine of claim 7 wherein the HA in the recombinant virus is modified at the HA cleavage site.

9. The vaccine of claim 1 wherein the recombinant influenza virus further comprises another attenuating mutation.

10. The vaccine of claim 1 that is formulated for intranasal delivery.

11. The vaccine of claim 1 wherein the amount of the attenuated virus in the vaccine is $10^3$ to $10^7$ PFU/kg.

12. A method to immunize a vertebrate, comprising:
administering to the vertebrate an effective amount of the vaccine of claim 1.

13. The method of claim 12 wherein the vertebrate is a human.

14. The method of claim 12 wherein the recombinant influenza virus has a HA that is H5 or H1.

15. The method of claim 12 wherein the vaccine is intranasally administered.

16. A method of making a dose of a vaccine, comprising:
providing a composition comprising live, attenuated isolated recombinant influenza virus comprising a mutant M gene segment that is mutated so that upon viral replication the mutant M gene expresses a functional M1 protein and a mutant M2 protein with a deletion of the cytoplasmic tail and either lacking a transmembrane domain or having a mutated transmembrane domain; and dispensing a portion of the composition into a receptacle in an amount of the live, attenuated isolated recombinant influenza virus effective to induce a protective immune response in a human.

17. The method of claim 16 wherein the HA in the attenuated isolated recombinant influenza virus comprises H5 HA.

18. The method of claim 16 wherein the receptacle further comprises at least two influenza viruses that are different from the attenuated isolated recombinant influenza virus.

19. The method of claim 16 wherein the attenuated isolated recombinant influenza virus is a reassortant virus.

20. The method of claim 16 wherein the amount is effective for intranasal delivery in a human.

21. The vaccine of claim 1 wherein the mutant M2 protein further comprises the heterologous protein at the C terminus of the extracellular domain.

22. The vaccine of claim 1 wherein the mutant M2 protein comprises the heterologous immunogenic protein of a pathogen.

23. The vaccine of claim 1 wherein the recombinant influenza virus comprises the heterologous HA.

24. The vaccine of claim 1 wherein the recombinant influenza virus comprises the heterologous NA.

25. The vaccine of claim 1 wherein the recombinant influenza virus comprises the heterologous HA and the heterologous NA.

26. The method of claim 16 wherein (a) the mutant M2 protein further comprises a heterologous protein at the C-terminus of the extracellular domain, (b) the mutant M2 protein further comprises a heterologous immunogenic protein of a pathogen, (c) the recombinant influenza virus comprises a hemagglutinin (HA) that is modified at the HA cleavage site, (d) the recombinant influenza virus further comprises another attenuating mutation, (e) the recombinant influenza virus comprises a HA that is a heterologous HA, or (f) the recombinant influenza virus comprises a neuraminidase (NA) that is a heterologous NA.

* * * * *

SEQUENCE LISTING

```
<160> NUMBER OF SEQ ID NOS: 16

<210> SEQ ID NO 1
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 1
gtgaatagaa ttggagtaaa aaactacc                                      28

<210> SEQ ID NO 2
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 2
tcaaaaatga ccatcgtcaa catccac                                       27

<210> SEQ ID NO 3
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 3
gtgagatggt cattttgtca acatagaa                                      28

<210> SEQ ID NO 4
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 4
tcaatccaca gcactctgct gttcctg                                       27
```

```
<210> SEQ ID NO 5
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 5
gtgacggcag gaacagcaga gtgctg                                          26

<210> SEQ ID NO 6
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 6
tcattccctc atagactcag gtacc                                           25

<210> SEQ ID NO 7
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 7
gtgagcaggg gtacctgagt ctatg                                           25

<210> SEQ ID NO 8
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 8
tcaaggccct cttttcaaac cgta                                            24

<210> SEQ ID NO 9
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 9
cttaaatacg gtttgaaaag agggcctgc                                       29

<210> SEQ ID NO 10
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 10
tcactcaata aatgcatttg aagaaaagac gatc                                 34

<210> SEQ ID NO 11
<211> LENGTH: 26
<212> TYPE: DNA
<213> ORGANISM: Artificial Sequence
<220> FEATURE:
<223> OTHER INFORMATION: A synthetic oligonucleotide
```

-continued

```
<400> SEQUENCE: 11
ttgttgttgc cgcaaatatc attggg                                      26

<210> SEQ ID NO 12
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 12
ttcactcaac ttgaatcgct gcatctgc                                    28

<210> SEQ ID NO 13
<211> LENGTH: 10
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 10
<223> OTHER INFORMATION: Xaa = Arg or Gly

<400> SEQUENCE: 13

Pro Gln Arg Glu Arg Arg Arg Lys Lys Xaa
1               5                   10

<210> SEQ ID NO 14
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 6
<223> OTHER INFORMATION: Xaa = Arg or Gly

<400> SEQUENCE: 14

Pro Gln Arg Glu Thr Xaa
1               5

<210> SEQ ID NO 15
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 15
ttcaagtgat cctctcacta ttgcc                                       25

<210> SEQ ID NO 16
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 16
ttcaagtgat actattgcc                                              19
```